United States Patent
Debreczeny et al.

(10) Patent No.: US 6,573,991 B1
(45) Date of Patent: Jun. 3, 2003

(54) SELF-COMPENSATING RADIATION SENSOR WITH WIDE DYNAMIC RANGE

(76) Inventors: Martin Paul Debreczeny, 310 Freitas Ct., Danville, CA (US) 94526; Michael Patrick O'Neil, 356 Morse Ave., Sunnyvale, CA (US) 94086; Athanasios Kasapi, 651 Castro St., San Francisco, CA (US) 94114

( * ) Notice: Subject to any disclaimer, the term of this patent is extended or adjusted under 35 U.S.C. 154(b) by 0 days.

(21) Appl. No.: 09/560,265

(22) Filed: Apr. 26, 2000

(51) Int. Cl.⁷ .............................................. G01N 15/02
(52) U.S. Cl. ...................... 356/336; 356/338; 356/337; 356/342; 356/343
(58) Field of Search ................................. 356/336, 335, 356/337, 338, 342, 343

(56) References Cited

U.S. PATENT DOCUMENTS

| | | |
|---|---|---|
| 3,976,891 A | 8/1976 | Parkinson |
| 4,017,193 A | 4/1977 | Loiterman |
| 4,769,550 A | 9/1988 | Dolnick |
| 4,981,362 A | 1/1991 | Dejong |
| 5,352,901 A * | 10/1994 | Poorman ............... 250/574 |
| 5,482,842 A | 1/1996 | Berndt |
| 5,483,080 A | 1/1996 | Tam |
| 5,497,769 A | 3/1996 | Gratton |
| 5,529,065 A | 6/1996 | Tsuchiya |
| 5,617,212 A | 4/1997 | Stuart |
| 5,831,730 A | 11/1998 | Traina |

FOREIGN PATENT DOCUMENTS

| | | |
|---|---|---|
| EP | 0945100 A1 | 9/1999 |
| WO | WO96/31764 | 11/1998 |

OTHER PUBLICATIONS

Wu, P.; Ozturk, S.S.; Blackie, J.D.; Thrift, J.C.; Figueroa, C.; Naveh, D. "Evaluation and Applications of Optical Cell Density Probes in Mammalian Cell Bioreactors", Biotechnology and Bioengineering, 1995, pp. 495–502, vol. 45, John Wiley and Sons, New York.

Junker, B.H.; Reddy, J.; Gbewonyo, K.; Greasham, R. "On–line and In–Situ Monitoring Technology for Cell Density Measurement in Microbial and Animal Cell Cultures", Bioprocess Engineering, 1994, pp. 195–207, vol. 10, Springer–Verlag, Berlin.

Ge, Z.; Cavinato, A.G.; Callis, J.B. "Noninvasive Spectroscopy for Monitoring Cell Density in a Fermentation Process," Analytical Chemistry, 1994, pp. 1354–1362, vol. 66, ACS, Washington, DC.

Konstantinov, K.B.; Pambuyan, R.; Matanguihan, R.; Yoshida, T. "On–Line Monitoring of Hybridoma Cell Growth using a Laser Turbidity Sensor", Biotechnology and Bioengineering, 1992, pp. 1337–1342, vol. 40, John Wiley and Sons, New York.

Harris, C.M.; Kell, D.B. "The Estimation of Microbial Biomass", Biosensors, 1985, pp. 17–84, vol. 1, Elsevier Applied Science Publishers, Ltd., England.

* cited by examiner

*Primary Examiner*—Frank G. Font
*Assistant Examiner*—Roy M. Punnoose

(57) ABSTRACT

A radiation sensing method and device that is used to measure physical properties of materials over a wide dynamic range. The sensor (20) comprises multiple radiation sources and multiple detectors at multiple separation distances. The detected signals from the different sources are separated and then combined mathematically in a manner such that the combination is self-compensated for both component drift and changes in radiation coupling efficiency between the source or detector and the material of interest. In a preferred embodiment, the biomass in a liquid cell culture (54) is measured with high accuracy over a wide dynamic range using optical wavelength radiation. The measurement can be made with the sensor external to the liquid culture container in a manner that is compensated for the thickness of the container window (50).

48 Claims, 17 Drawing Sheets

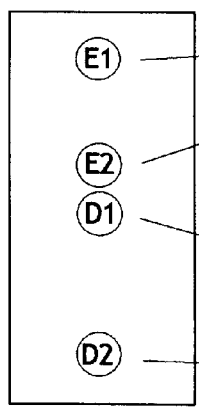
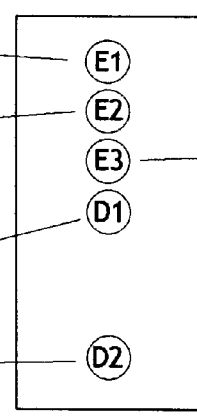
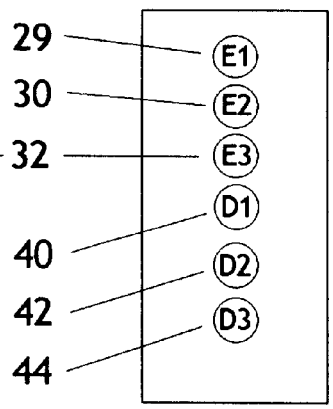
Fig. 3a     Fig. 3b     Fig. 3c
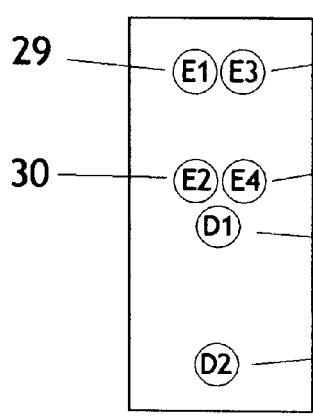
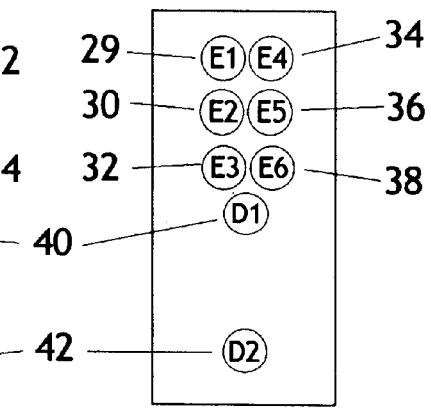
Fig. 3d     Fig. 3e

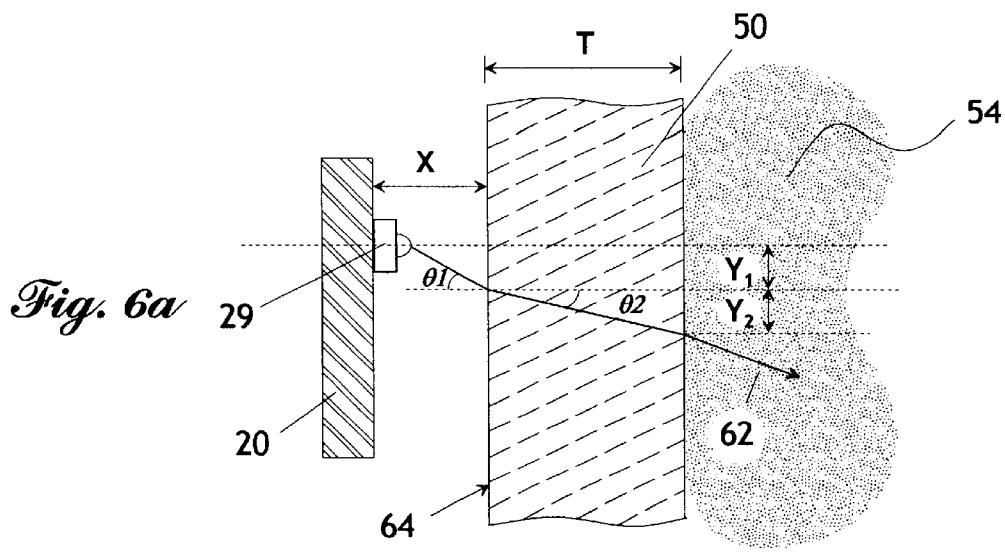
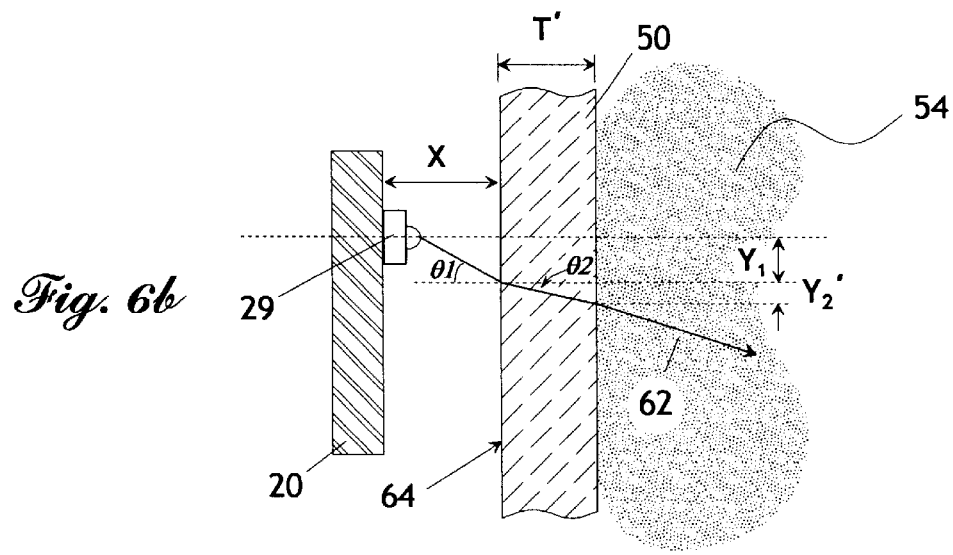
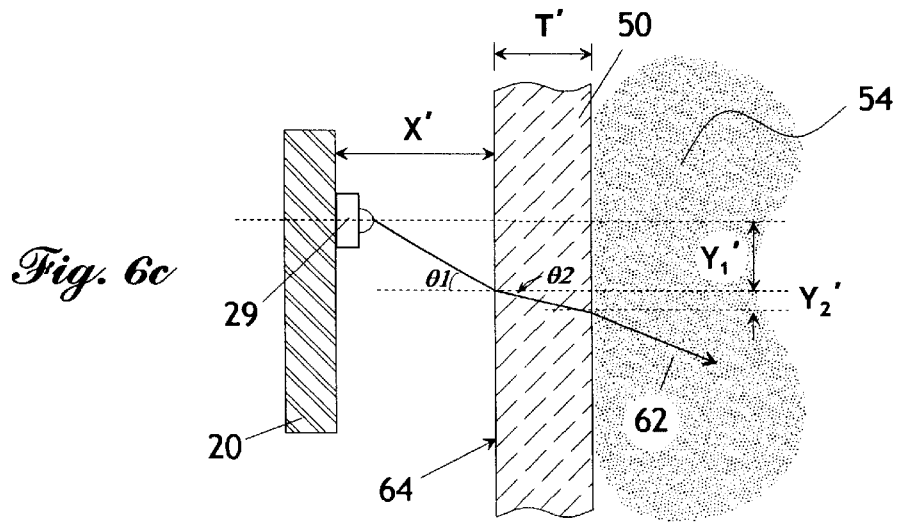

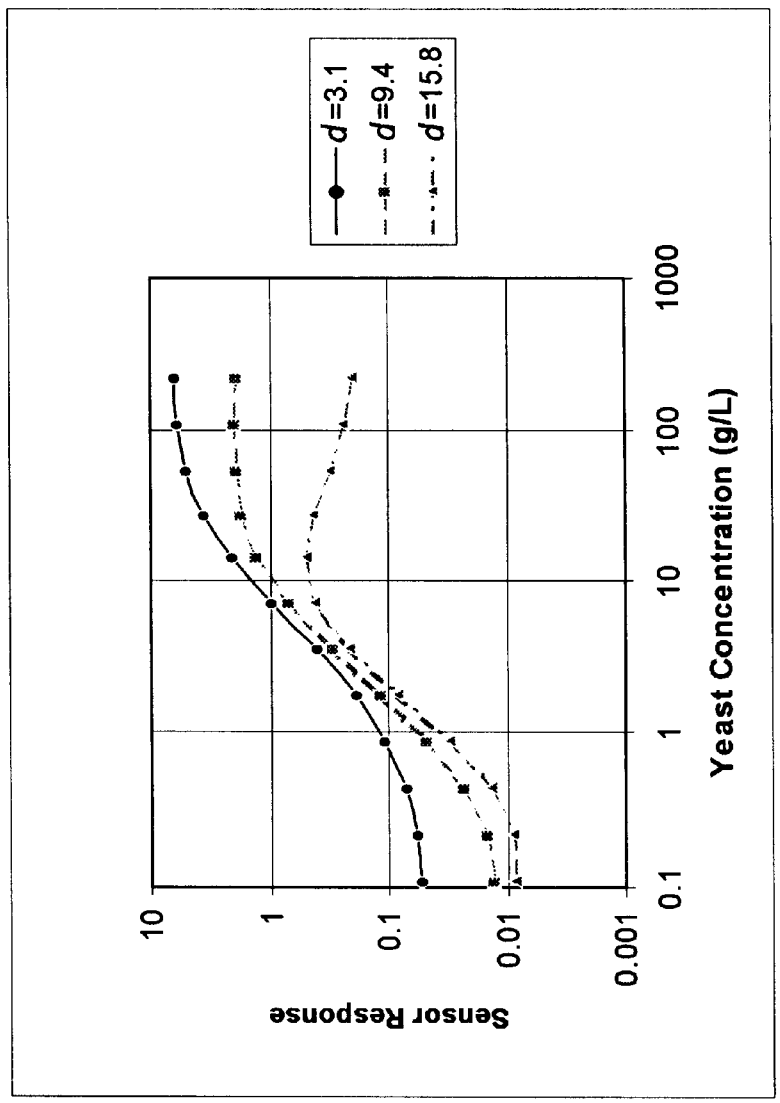
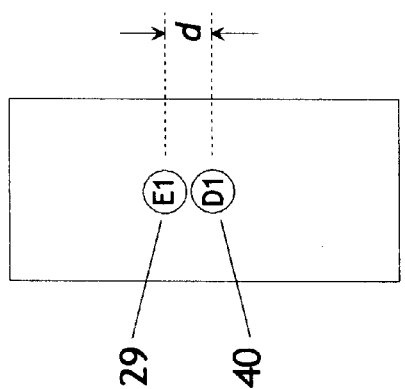
Fig. 9a (Prior Art)

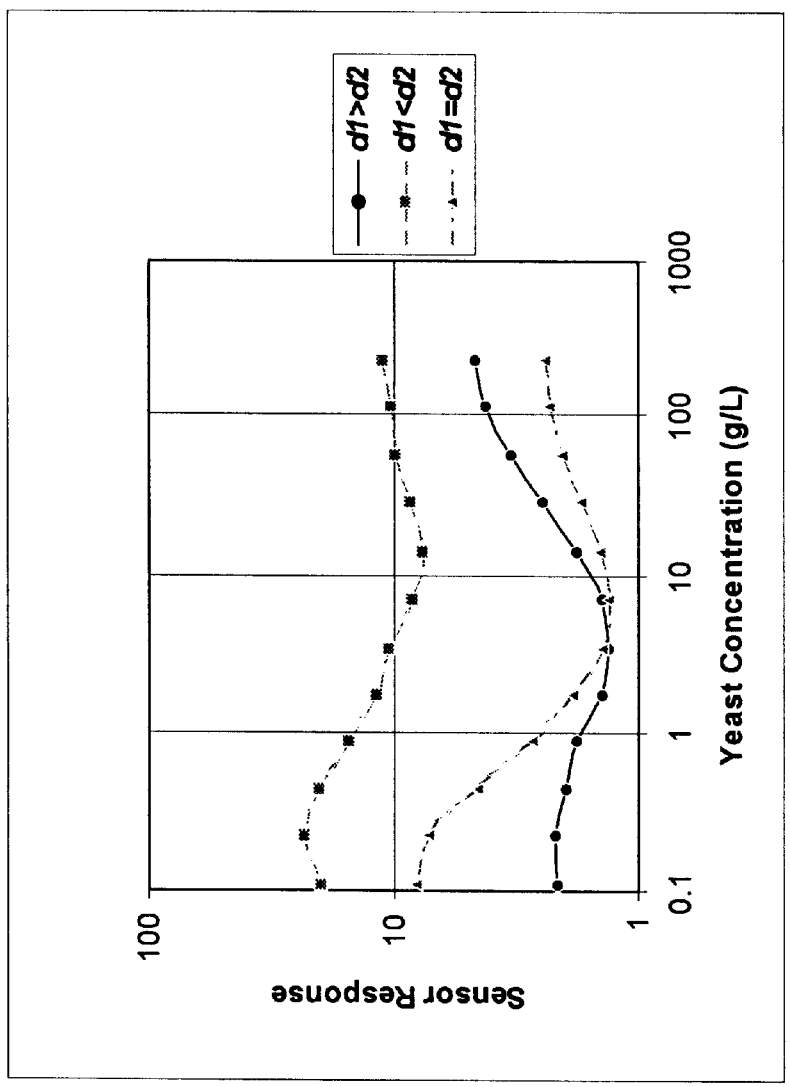
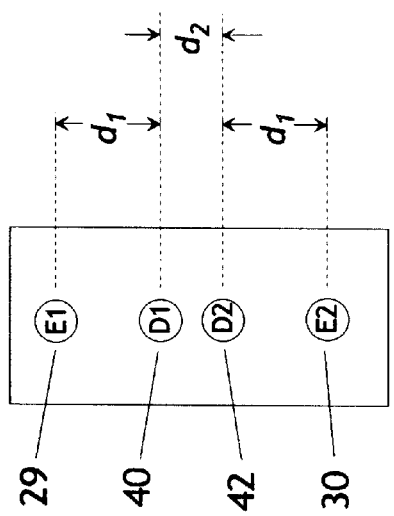
Fig. 9b (Prior Art)

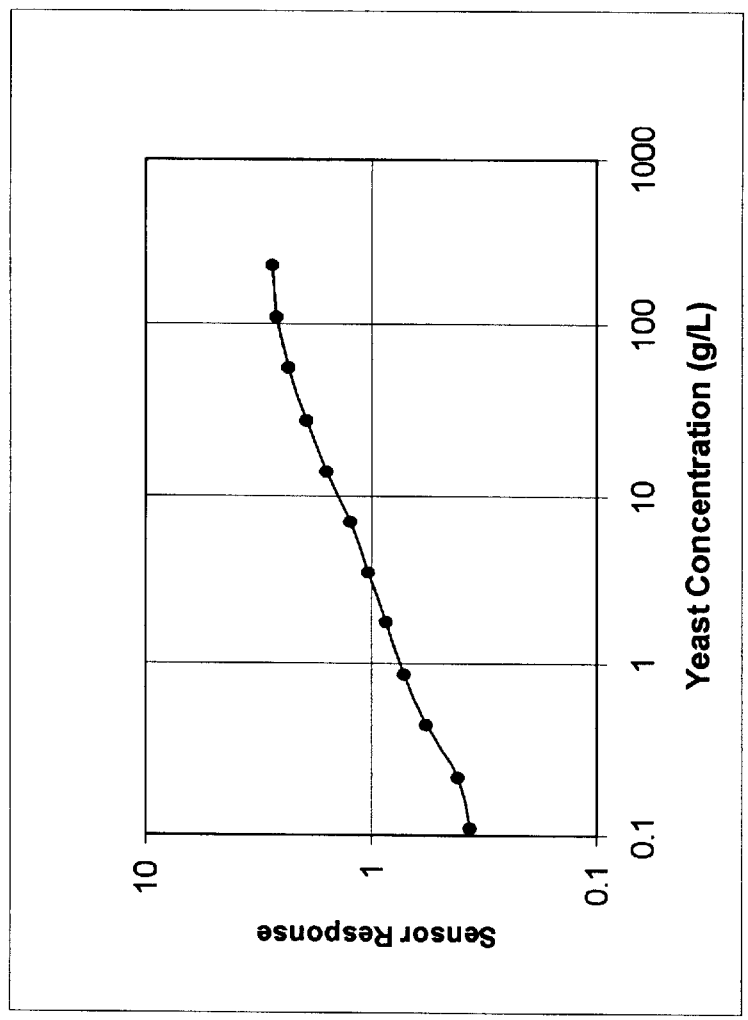
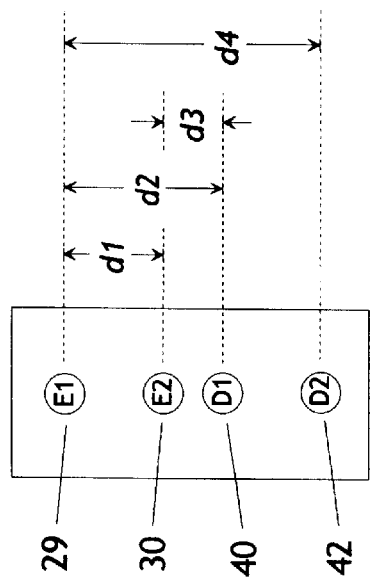
Fig. 9c

SELF-COMPENSATING RADIATION SENSOR WITH WIDE DYNAMIC RANGE

CROSS REFERENCE TO RELATED APPLICATIONS

Not applicable.

BACKGROUND

1. Field of the Invention

The present invention relates generally to methods and devices for determining properties of a medium using radiation sensors that are compensated for component drift and changes in radiation coupling to the medium. A specific embodiment of the invention relates to biomass monitoring, where radiation scattering is used to measure the concentration of cells or microorganisms in liquid cultures.

2. Description of Prior Art i. Compensated Radiation Sensors

Radiation sensors are widely used in the analysis of material properties. In particular, the absorption and scattering of radiation, measured by means of a radiation sensor, can be related to the concentration of a particular material within a mixture. Such measurements can be made rapidly and free from the risk of consuming, infecting, or damaging the material being analyzed. Some examples of commercial applications of optical radiation sensors are: smoke detectors, stack emission sensors, tissue oxygenation sensors, and biomass monitors in liquid cultures of cells or microorganisms.

Two common difficulties with radiation sensors that have been addressed in prior art, but not adequately resolved in combination, are sensor drift and limited dynamic range. Drift of sensor response can result from of any of the following: (1) a change in source intensity, (2) a change in detector sensitivity, and (3) a change in the efficiency of radiation coupling between the sensor and the sample. As radiation sources and detectors age, their respective output and sensitivity inevitably change. These aging effects can lead to inaccuracy in the determination of the property of the material being analyzed. The third source of sensor drift can be particularly prevalent in sensors that monitor harsh, dirty, or biologically active environments such as in the above examples of stack emission monitoring and biomass monitoring of liquid cultures. In both of these examples, accumulation of matter on the surface of the sensor can lead to drift or inaccurate readings of the sensor.

The dynamic range of material properties that can be measured by many radiation sensors is limited by the non-linear relationship between concentration of the material and attenuation of the radiation. For differing concentrations of an absorbing or scattering material of interest, the radiation level impinging upon the sensor will vary widely; high concentrations of material will greatly attenuate the radiation compared to low concentrations. For this reason, sensors that measure the transmission of radiation through a single fixed path length of material will have an inherently narrow dynamic range over which material properties can be measured.

U.S. Pat. No. 3,976,891—Parkinson discloses a sensor for smoke detection that compensates for changes in the optical coupling efficiency between the sensor and medium of interest by comparing the light transmitted through two different path lengths of air to two different detectors. The disadvantage of this method is that it provides no compensation for light source or detector drift. Further, the dynamic range of the measurement is limited by its reliance on only light transmittance to determine smoke density.

U.S. Pat. No. 4,981,362—deJong discloses a particle concentration measuring method employing a single light source and detector. Light is transmitted from the source to the detector through a movable window. By computing the ratio of the light transmitted through the window at two different path length settings, light source, detector, and optical coupling drift are partially compensated. However, any instrumental drift that occurs between the two measurements will not be compensated. Another disadvantage of this method is that it requires the use of a moving part whose mechanical motion and physical manufacture must be highly reproducible in order to compare measurements made at different times or with different devices. This method also suffers from limited dynamic range due to reliance on only light transmittance to determine particle concentration.

U.S. Pat. No. 5,617,212—Stuart describes an apparatus for open-path gas monitoring that measures transmission of light between two sources and two detectors. The second source is for calibration purposes only and does not pass through the sample. Likewise, the second detector is used only for calibration and measures light from the two sources that does not pass through the samples. This method provides the advantage of compensating for light source and detector drift. However, it does not provide compensation for changes in optical coupling efficiency between the sensor and sample. In addition, this method suffers from both limited sensitivity and dynamic range due its use of only light transmittance to measure the gas density.

U.S. Pat. No. 5,497,769—Gratton describes a sensor employing multiple light sources and a single detector. U.S. Pat. No. 5,529,065—Tsuchiya describes a sensor employing a single light source and multiple detectors. Both patents describe the measurement of light diffusely reflected from highly scattering materials. The disadvantage of these methods is that they require frequent re-calibration to compensate for light source and detector drift. In addition these methods are prone to error due to changes in the optical coupling efficiency between the sensor and sample.

U.S. Pat. Nos. 4,017,193—Loiterman and U.S. Pat. No. 5,482,842—Berndt, and European Patent Application 0945100A1—Hueber describe sensors employing two light sources and two detectors arranged to provide a pair of equal-length long paths and a pair of equal-length short paths between light sources and detectors. The four signals provided by these four combinations of sources and detectors are combined in a manner that compensates for drift in light source intensity, detector sensitivity, and efficiency of optical coupling between the sensor and the sample. The methods described by Loiterman and Berndt involve transmitting light through gaseous materials and detecting the extent of scattering or absorption, respectively. The method described by Hueber involves the detection of diffusely reflected light from a highly scattering medium such as tissue. The critical disadvantage of all three of these methods is the limited dynamic range over which material properties can be measured due to the geometric constraint that there be only two unique path lengths between light sources and detectors.

ii. Measurement of Biomass in Liquid Cultures

Liquid cultures of cells or microorganisms are frequently grown for research purposes or for commercial gain. Cells or microorganisms can be genetically modified to produce high yields of chemicals that may be difficult, expensive, or impossible to synthesize by other means. In order to prevent growth of other undesirable cells or microorganisms in the same liquid culture, it is important that the culture be grown under sterile conditions. For this reason, the growth medium is sterilized prior to inoculation with the desired cell or microorganism. In order to maintain a barrier to foreign organisms and optimize the growth of the desired cell or microorganism, liquid cultures are frequently grown under highly controlled conditions in what are referred to as fermenters or bioreactors. In addition to maintaining sterile conditions, fermenters may provide control over such parameters as temperature, pH, rate of stirring, and concentration of nutrients and dissolved gases.

Cells or microorganisms typically undergo several stages of growth in a fermenter. After inoculation, the initial growth rate of the cells or microorganisms may be slow, as the organism becomes accustomed to the new environment. This is frequently followed by a rapid growth phase where the biomass increases nearly exponentially. This growth period is sometimes referred to as the "log phase" due to the fact that the change in the logarithm of biomass is nearly linear with time. Eventually, as the nutrient supply relative to the biomass diminishes, the growth will slow. In order to achieve maximum biomass, the conditions in the fermenter need to be changed during the different phases of growth. Ideally a feedback mechanism would link the measured growth of the cells or microorganisms to the conditions in the fermenter. Frequently, a physical or chemical stimulus is used to induce production of a desired chemical by the cells or microorganisms. The timing of this induction relative to the growth cycle of the cells or microorganisms is often critical in order to achieve maximum chemical yield. Unfortunately, methods of continuously and reliably measuring the growth of cells or microorganisms in liquid cultures are not widely available.

The most commonly used method of measuring the biomass in liquid cultures is by extracting a portion of the liquid and measuring its optical density with a spectrophotometer. This method has several disadvantages: (1) each time liquid is withdrawn, there is a risk that the culture will be contaminated, (2) the method is not continuous, and (3) the method is labor intensive, requiring frequent extraction and precise volumetric dilution of the extracted liquid when high cell concentrations are measured. Commercial devices are available (eg. Wedgewood Technology, Incorporated, Model 650 "Absorbance Monitor") that offer continuous measurement of optical density using a probe that is immersed in the liquid culture. Unfortunately, such devices are prone to drift (see above discussion of compensated radiation sensors), particularly due to growth of cells or microorganisms on the sensor itself In addition, the range of biomass that can be measured is severely limited by the use of fixed path length transmission measurements. Many microorganisms, particularly strains of yeast (e.g. Pichia Pastoris), are grown to much higher concentrations (e.g. 50 g/L and higher) than can be measured with any known commercially-available device based on optical transmittance.

U.S. Pat. No. 5,483,080 —Tam describes a method for measuring biomass in liquid cultures using optical reflectance. The method restricts the source or detector to be singular in number. By measuring the light that is diffusely reflected back from the liquid culture, the method gains an advantage in the range of cell densities that can be measured, compared to transmission methods. However, the sensor output is highly non-linear with change in concentration or the logarithm of concentration of cells or microorganisms. In one embodiment the effect of detector drift is compensated by calculating a ratio of the light detected from two light sources. However, this method does not compensate for light source drift or for changes in efficiency of optical coupling between the sensor and sample. One embodiment of this invention is a sensor designed to be immersed in a liquid culture. Growth of cells or microorganisms on the surface of the sensor may lead to changes in sensor response that do not accurately reflect the suspended cell concentration. No means is provided to compensate for this effect. A second embodiment of this invention is a sensor mounted to the exterior of a container holding a liquid culture. The container is assumed to have a window that is transparent to the light source. This non-contact method provides the advantage that the sensor does not need to be sterilized. However, no means is provided to compensate for optical imperfections in the container wall, either inherent to the window or as caused by the growth of cells or microorganisms on the interior of the window over time. In addition, the invention provides no method of compensating for the variable glass thickness that is observed between different types of growth vessels. A specific calibration would need to be provided for each type of vessel on which the method is practiced.

SUMMARY OF THE INVENTION

The present invention provides a radiation sensing method and device that can be used to measure physical properties of materials over a wide dynamic range. The measurements are self-compensated for both component drift and changes in radiation coupling efficiency between the sensors and the material of interest. The invention finds particular utility in measuring biomass in liquid cell cultures with high accuracy over a wide dynamic range. The measurement can be made with the sensor external to the liquid culture container in a manner that is compensated for the thickness of the container window.

OBJECTS AND ADVANTAGES

Accordingly, several objects and advantages of the present invention are:
a) the measured values of the physical properties being determined are compensated for fluctuations or the effects of aging on the source radiation intensity,
b) the measured values of the physical properties being determined are compensated for fluctuations or the effects of aging on the detector sensitivity,
c) the measured values of the physical properties being determined are compensated for dirt or other materials or conditions that effect the interface between the sensor and the material of interest,
d) the necessity of using moving parts to confer advantages a) through c) is eliminated, and
e) the physical properties are measurable over a wider dynamic range compared to other radiation sensing methods that confer advantages a) through d).

Additional objects and advantages of the present invention for the specific embodiment in which the radiation sensor is used to measure particle concentration in scattering media:
a) the radiation sensor output provides a more linear response to changes in the logarithm of concentration than do radiation sensors described in prior art, and
b) the sensor output is compensated for the accumulation of particles at the interface between the sensor and the scattering medium, and c) the concentration of multiple particle types and/or the particle size distribution of particular particle types may be simultaneously measured.

Additional objects and advantages of the present invention for the specific embodiment in which the sensor is mounted externally to a container holding a liquid culture for the purpose of measuring the biomass:

a) the need to sterilize the sensor and its housing are eliminated, b) the sensor housing can be constructed for lower cost than sensor housings requiring sterilization and immersion in a liquid culture, c) the risk of contaminating the liquid culture with foreign matter is eliminated, d) multiple different fermenters can be monitored with the same sensor without interrupting the growth of the cultures or risking exposure of the cultures to foreign matter, and e) the measured value of the biomass in the liquid culture is compensated for variations in window thickness between different fermenters.

Further objects and advantages of the present invention will become apparent from a consideration of the drawings and ensuing description.

BRIEF DESCRIPTION OF THE DRAWINGS

In the drawings, closely related figures have the same number but different alphabetic. suffixes.

FIGS. 3a to 3e show various possible arrangements of the radiation sources and detectors that comprise a self-compensating radiation sensor.

FIGS. 6a to 6c illustrate how the effect of variable fermenter window thickness can be compensated by the use of a variable air gap between the sensor and the external surface of the window.

FIGS. 9a and 9b show sensor configurations described in prior art and the experimentally measured output from these sensors as a function of yeast concentration. FIG. 9C shows a preferred sensor configuration of the present invention (from FIG. 3A) and the experimentally measured output from the self-compensating sensor of the present invention as a function of yeast concentration.

Reference Numerals in Drawings

Figure 1:
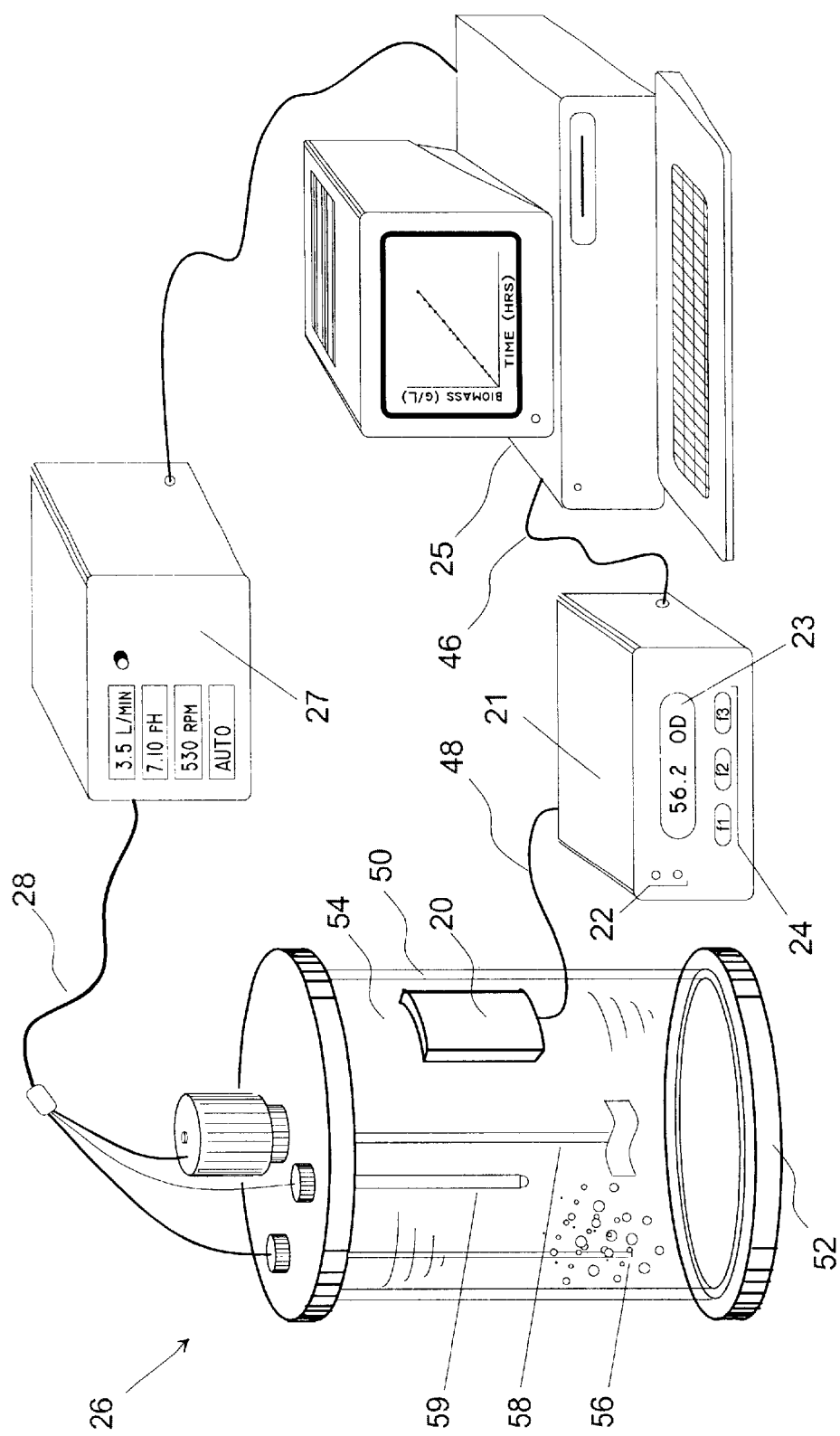
FIG. 1 shows a radiation sensor mounted on the exterior surface of a fermenter and integrated into an instrument designed to continuously monitor the biomass suspended in a liquid culture.

| 20 | radiation sensor | 21 | sensor controller |
|----|------------------|----|-------------------|
| 22 | sensor indicators | 23 | sensor controller display |
| 24 | sensor controller buttons | 25 | processor |
| 26 | fermenter | 27 | fermenter controller |
| 28 | fermenter controller cable | 29 | first radiation source |
| 30 | second radiation source | 32 | third radiation source |
| 34 | fourth radiation source | 36 | fifth radiation source |
| 38 | sixth radiation source | 40 | first detector |
| 42 | second detector | 44 | third detector |
| 46 | sensor controller cable | 48 | sensor cable |
| 50 | window | 52 | container |
| 54 | liquid culture | 55 | dissolved oxygen sensor |
| 56 | bubbling device | 58 | stirring device |
| 59 | pH sensor | 60 | sensor mount |
| 61 | plate | 62 | light ray |
| 64 | external window surface | 66 | adhesive |
| 68 | legs | 70 | sensor housing |

DETAILED DESCRIPTION OF THE INVENTION

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments and may be satisfactorily applied for the measurement of any material which may exhibit similar behavior that are also intended to be encompassed within the spirit and scope of the invention.

The detailed description set forth herein will make reference to the measurement of biomass in a liquid culture. The term "biomass" as used in this patent application, refers to the concentration of biological material, such as cells or microorganisms. What is meant here and elsewhere in the patent application by "concentration" is the number of a type of particle, weight of a type of material, or volume of a type of material found in a given volume of a medium.

The method(s) and instrument(s) of the present invention may also find application in liquid suspensions of solids other than biomass as well as in solutions. For example, the particulate content in milk, the rate of polymerization in a chemical system or the turbidity of water may be measured by application of the method(s) and/or instrument(s) of the present invention. Similarly, the present invention may be utilized to determine the amount of gas in a liquid phase, such as the concentration of gas bubbles in a liquid medium. In addition, the attenuation of radiation by absorption may be used to measure the concentration of components dissolved in solution, by application of the present invention.

The method and instruments of the present invention may also be useable in the gas phase. For example, in industrial plants using smokestacks, the amount or concentration of a specific component of the effluent gas may be measured by application of the present invention. As another example, the present invention may be used to measure the particulate content of a gas for the purpose of smoke or fire detection. As yet another example, the present invention may be used to measure the concentration of a particular component of a gas, such as the concentration of carbon dioxide in a mixture of gases or the density of fog or smoke in the flight path of an airplane.

In addition, the method(s) and/or instrument(s) of the present invention may be utilized to monitor materials in the solid state and to monitor transformation of materials between states. For example, the present invention may be used to measure the concentrations of oxygenated and deoxygenated hemoglobin in tissue. As another example, the present invention may used to monitor the conversion of a liquid to the solid state, such as gel formation. Thus, although the hereinafter-set-forth description refers specifically to the measurement of the biomass in a liquid culture, it will be appreciated that the method(s) and instrument(s) of the present invention are also applicable in other liquids and in gas and solid media applications.

DESCRIPTION OF THE PREFERRED EMBODIMENT

A preferred embodiment of the present invention is illustrated in FIG. 1. A radiation sensor 20 is mounted to the exterior of a container 52 used for fermentation of liquid cultures 54 of cells or microorganisms. The sensor is mounted to a surface of the container that provides a window through which radiation can pass into the liquid culture. The window need not be a specially prepared surface. For example, in a fermenter 26 that uses glass as the containment vessel, any surface of the container may serve as the window. However, the preferred placement of the sensor is in a region of the vessel that is relatively free from reflections from devices immersed in the liquid culture such as stirring devices 58, gas sparging devices 56, pH sensors 59, etc. Further, the preferred placement of the sensor is away from the top of the container where the liquid culture interfaces with air.

Figure 2:
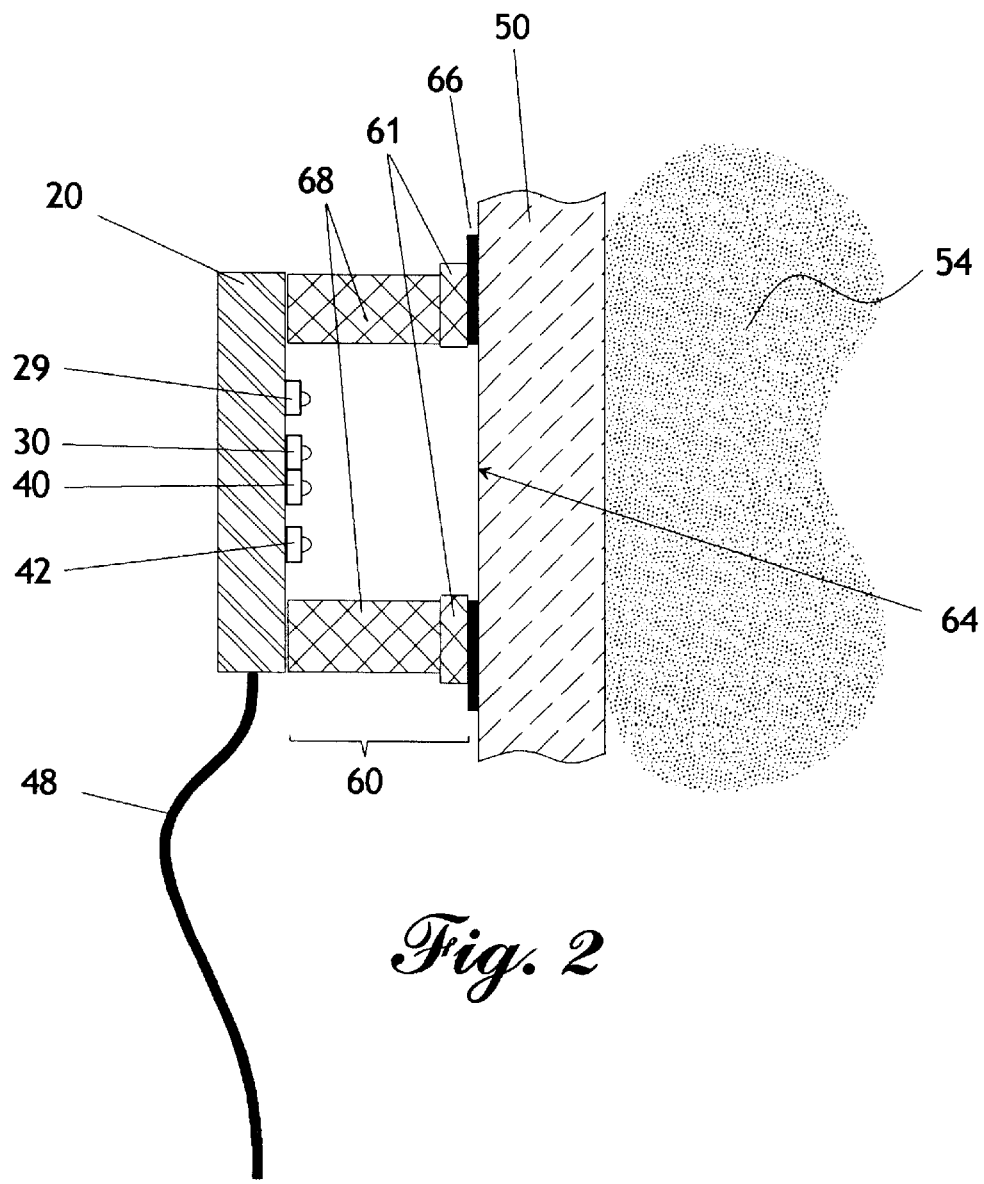
FIG. 2 shows a cross-sectional view of a radiation sensor mounted on the exterior surface of a fermenter.

The sensor is held against the window of the fermenter using a sensor mount 60 such as that shown in cross-section in FIG. 2. The sensor mount consists of a plate 61 that adheres to or is mechanically brought into contact with the surface 64 of the window 50. The adhesion may be accomplished by such means as adhesives, two-sided adhesive tape, or suction. Mechanical contact may be achieved with a strap which encircles the fermentor or other clamping means. The present preferred method of adhesion is double-sided tape 66. Legs 68 of variable length are attached to the plate. The variable length of the legs compensates for variable window thickness, as is explained further in the section below entitled "Compensation for Window Thickness". The radiation sensor 20 is coupled to the legs. In the currently preferred embodiment, this coupling is magnetic. The gap between the sensor and the window may be left open to air or filled with a material whose index of refraction matches that of the window material. In the currently preferred embodiment the gap is left open to air. The sensor comprises a housing, a plurality of radiation sources and detectors, and electronic circuitry. A preferred sensor arrangement containing two radiation sources and two detectors is depicted in FIG. 3a. The radiation sources (29 and 30) and detectors (40 and 42) are centered along a straight line in the following order: first radiation source 29, second radiation source 30, first detector 40, second detector 42, where the respective distances between each of these components in the currently preferred embodiment is 6.3 mm, 3.1 mm, and 6.3 mm. However, many other geometric arrangements of the radiation sources and detectors will also be suitable. In order to measure the concentration of microorganisms over a wide dynamic range, the sensor geometry must provide at least three unique distances from the radiation sources to the detectors. The currently preferred radiation sources are vertical cavity surface-emitting lasers (VCSELs), emitting light at 850 nm with 6 degree divergence angle (Honeywell, part no. SMV2637-001). However, many other radiation sources that emit radiation in the ultraviolet, visible, infrared, microwave, and millimeter wave regions of the spectrum may also be suitable. For example, laser diodes or light emitting diodes (LEDs) may serve as suitable radiation sources. The active area of the currently preferred detectors is made from silicon and is approximately 1.3 mm×1.3 mm (Hamamatsu Photonics, model no. S2164). Many other detector sizes and types could also be used. For example, for detection of near infrared light at wavelengths greater than 1000 nm, detectors containing Indium Gallium Arsenide (InGaAs) as the active element could be used.

Figure 4A:
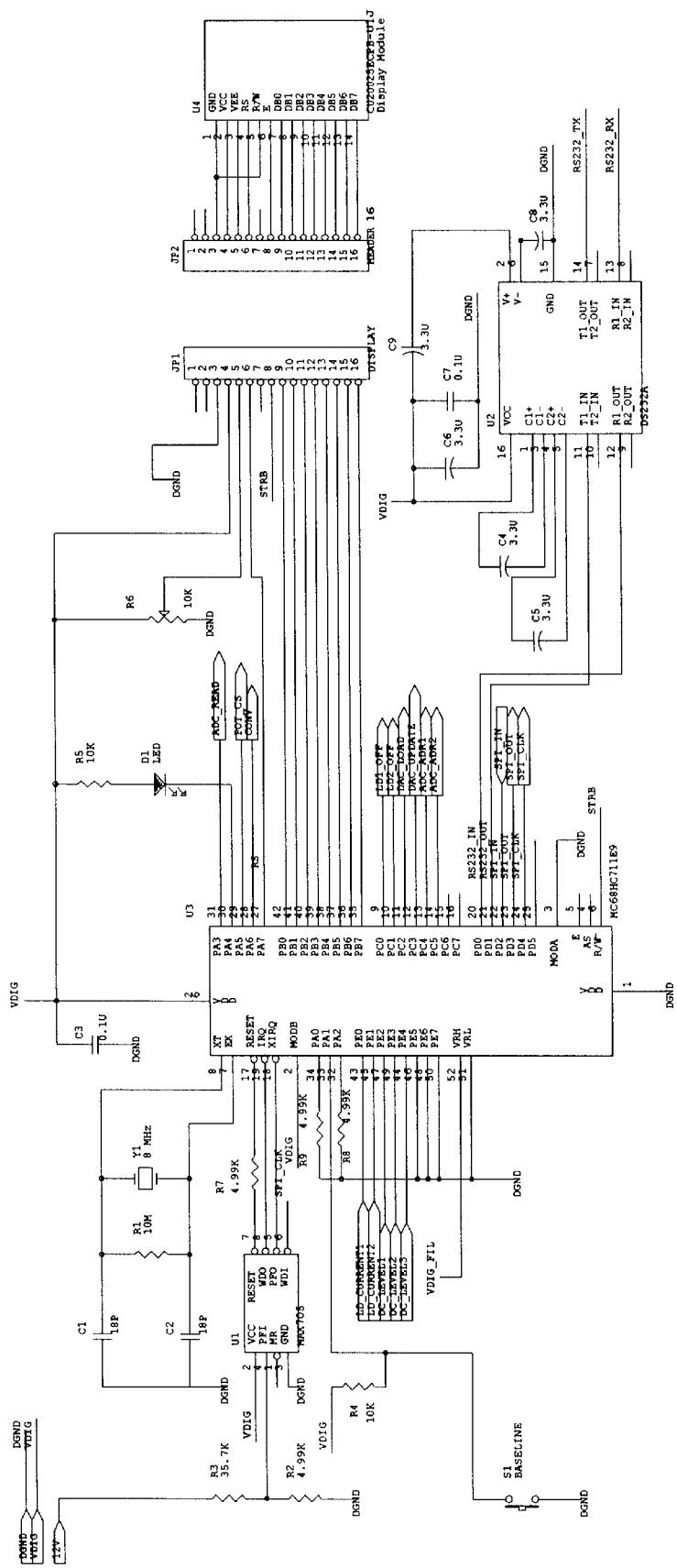
FIG. 4a is a schematic of the electronic circuit used in the radiation sensor.

An example schematic of the electronic circuitry used in the sensor is shown in FIG. 4a. Many other electronic circuits and specific components could be substituted for those shown in FIG. 4a while remaining within the scope of the present invention.

Referring back to FIG. 1, a sensor cable 48 connects a controller 21 to the radiation sensor 20. The sensor controller contains the following components: (a) electronic circuitry to process the detected signals, (b) electronic circuitry to control the intensity of the radiation sources and the gain of the amplifiers in the sensor, (c) a power supply for the electronic circuitry, (d) an RS-232 interface that allows the sensor controller to communicate with a processor, (d) a sensor controller display 23 for displaying a value that is related to the biomass in the liquid culture, (e) sensor indicators 22 that indicate the operating state of the sensor, and (f) sensor controller buttons 24 that allow the user to interactively control the operation of the sensor controller. Example schematics of the electronic circuitry that could be used in the sensor controller are shown in FIGS. 4b to 4e. Again, these schematics are meant to provide but one example of the many electronic configurations and components that could be used to implement the present invention. For example, the sources and detectors could be replaced by microwave or acoustic devices, with appropriate signal conditioning and computation.

The sensor may be operated in stand-alone mode using only the controller or the controller may be interfaced to a processor 25. The sensor controller is connected to the processor with a sensor controller cable 46. In the currently preferred embodiment, the processor is a personal computer that may include a central processing unit, a monitor for displaying results, and a keyboard and mouse for interactive user control. The processor may also be interfaced to a fermenter controller 27 using a fermenter controller cable 28. The cables used to connect the sensor, controllers, and processor could be eliminated if a remote communication method, such as radio waves or infrared radiation, were employed instead.

THEORY AND OPERATION OF THE PREFERRED EMBODIMENT

In the preferred embodiment illustrated in FIG. 1, a radiation sensor 20 is used to measure the biomass in a liquid culture 54. Radiation emitted from multiple sources in the sensor passes through a window of a container 52 filled with the liquid culture of cells or microorganisms. The radiation is scattered multiple times by the cells or microorganisms, creating a "glow ball" of radiation within the culture. The intensity and size of the glow ball are dependent on the biomass within the liquid culture. At early stages of growth, when the biomass is low, the glow ball will be large in size and weak in intensity. As the cells or microorganisms grow and divide, the biomass will increase and the glow ball will reduce in size and increase in intensity. The detectors in the sensor are sensitive to the intensity of radiation emanating from the glow balls. Further, the sensor is arranged such that there are at least three separation distances between the detectors and radiation sources (see FIGS. 3a to 3e). Each of the detectors is sensitive to the glow ball generated from the radiation emitted by each of the sources. In this way, not just the intensity but the size of the glow ball is measured. By combining the signals from the multiple detectors due to the multiple radiation sources, the biomass in the liquid culture is accurately determined with a wide dynamic range.

Compensation for Radiation Source Intensity, Detector Gain, and Radiation Coupling Efficiency In addition to providing sensitivity to a wide range of concentrations, the multiple detected signals are combined in such a way that the combined result is compensated for changes in radiation source intensity, detector sensitivity, and radiation coupling efficiency between the sensor and the liquid culture. Referring to FIG. 3a, the signals detected by the first detector 40 and the second detector 42 are each further separated according to whether the detected radiation originated from the first radiation source 29 or the second radiation source 30. These four signals are then combined according to the equation:

$$R = \frac{S_{E1D1}S_{E2D2}}{S_{E1D2}S_{E2D1}} \quad \text{(eq. 1a)}$$

or its inverse:

$$R = \frac{S_{E1D2}S_{E2D1}}{S_{E1D1}S_{E2D2}} \quad \text{(eq. 1b)}$$

where:

$S_{E1D1}$ is proportional to the intensity of radiation from the first radiation source that is detected at the first detector;

$S_{E2D2}$ is proportional to the intensity of radiation from the second radiation source that is detected at the second detector;

$S_{E1D2}$ is proportional to the intensity of radiation from the first radiation source that is detected at the second detector; and $S_{E2D1}$ is proportional to the intensity of radiation from the second radiation source that is detected at the first detector.

As shown in eq. 2, each of the signals, S, used to compute the combined result, R, is dependent on the intensity of the radiation source, I, the sensitivity of the detector, Q, the efficiency with which the radiation source is coupled into the liquid culture, $\epsilon_E$, the efficiency with which the radiation is captured by the detector, $\epsilon_D$, and a radiation transfer function, $f$.

$$S = I_E \cdot Q_D \cdot \epsilon_E \cdot \epsilon_D \cdot f(\lambda, r) \quad \text{(eq. 2)}$$

The radiation transfer function is dependent on the wavelength of radiation emitted by the radiation source, $\lambda$, the separation distance, r, between the source and the detector, and the scattering and absorbing behavior of radiation in the medium from which the parameters of interest are ultimately determined. The result of substituting the representation of the detected signals given by eq. 2 into eq. 1a is:

$$R = \frac{I_{E1} \cdot Q_{D1} \cdot \varepsilon_{E1} \cdot \varepsilon_{D1} \cdot f(\lambda_{E1}, r_{E1D1}) \cdot}{I_{E1} \cdot Q_{D2} \cdot \varepsilon_{E1} \cdot \varepsilon_{D2} \cdot f(\lambda_{E1}, r_{E1D2}) \cdot} = \frac{I_{E2} \cdot Q_{D2} \cdot \varepsilon_{E2} \cdot \varepsilon_{D2} \cdot f(\lambda_{E2}, r_{E2D2})}{I_{E2} \cdot Q_{D1} \cdot \varepsilon_{E2} \cdot \varepsilon_{D1} \cdot f(\lambda_{E2}, r_{E2D1})}$$

$$\frac{f(\lambda_{E1}, r_{E1D1}) \cdot f(\lambda_{E2}, r_{E2D2})}{f(\lambda_{E1}, r_{E1D2}) \cdot f(\lambda_{E2}, r_{E2D1})}$$

(eq. 3)

From the second equality in eq. 3, it can be seen that the combined result, R, is dependent only on the radiation transfer function; R is independent of the intensity of the radiation sources, the sensitivity of the detectors, and the radiation coupling efficiency between the sensor and the liquid culture.

Figure 7:
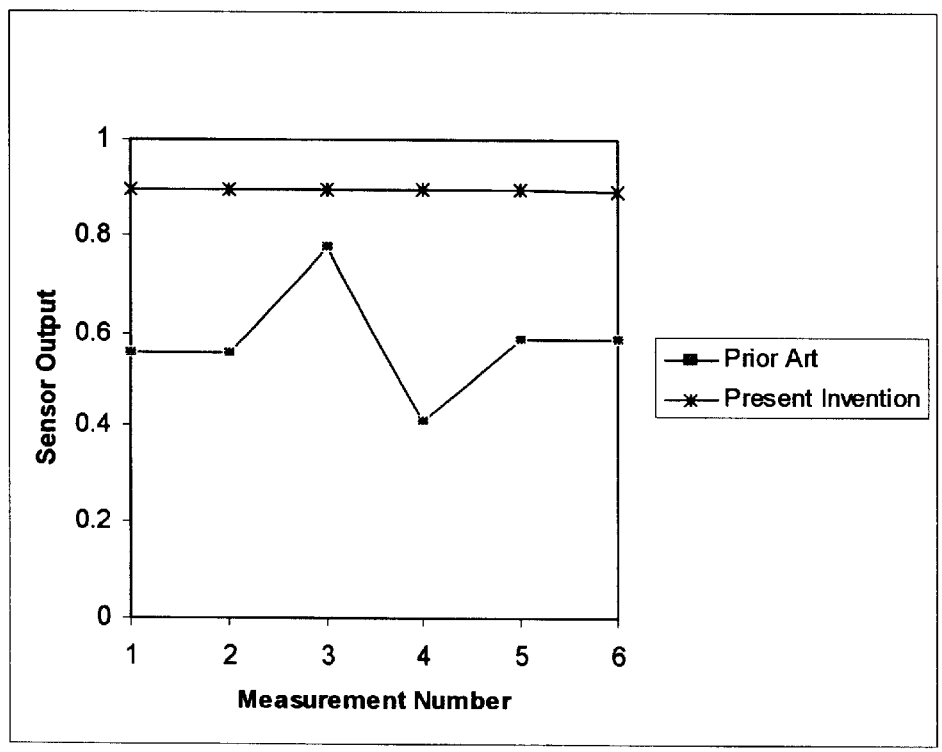
FIG. 7 is a graphical illustration of the insensitivity to changes in detector gain of the combined result from the self-compensated radiation sensor of this invention, as compared to the signal from a radiation sensor consisting of a single light source and detector pair provided in prior art.
Figure 8:
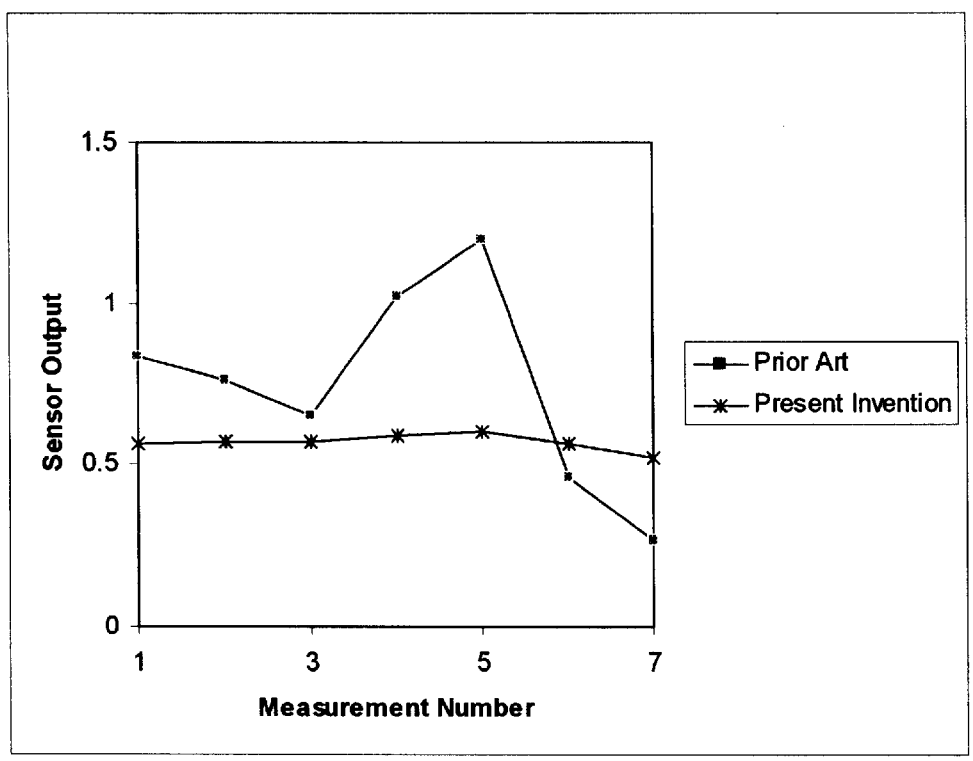
FIG. 8 is a graphical illustration of the insensitivity to changes in source intensity of the combined result from the self-compensated radiation sensor of this invention, as compared to the signal from a sensor consisting of a single light source and detector pair provided in prior art.

The graphs shown in FIGS. 7 and 8 demonstrate that the theoretical advantages described above are born out in the practice of the present invention. FIG. 7 shows the signal output from a mixture of milk and water using a sensor consisting of a single radiation source (LED emitting at 660 nm) and a single detector (1.3×1.3 mm silicon) as provided in prior art. The gain of the detector varies as a function of time. This change in gain is directly reflected in the sensor output. In contrast, using the same liquid culture and range of detector gain, with a sensor consisting of two radiation sources (two LEDs emitting at 660 nm) and two detectors (both 1.3×1.3 mm silicon) and combining the signals according to eq. 1, the sensor output shows insensitivity to changes in the gain of the detectors. Similarly, FIG. 8 shows the signal output from a mixture of milk and water when the radiation source intensity varies over time. The signal from a sensor consisting of a single radiation source and detector varies in direct proportion to the changes in radiation intensity, whereas the combined result from a sensor consisting of two radiation sources and two detectors is much less sensitive to radiation source intensity variation.

The advantage of computing the sensor output using eq. 1 goes beyond compensating for unintended passive fluctuations in radiation source intensity and detector gain. Instead, in the preferred embodiment of the present invention, the intensity and gain are dynamically optimized in order to increase the sensitivity of the biomass measurement. The intensity of scattered radiation that returns to the detector can vary over many orders of magnitude as a function of the biomass in the liquid culture. If the radiation source intensity and detector gain were fixed and optimized, for example, to provide maximum signal levels at high concentrations of cells or microorganisms, then at low concentrations the signal would be too weak to differentiated from electrical noise. In the present invention, the radiation source intensity and detector gain are varied without affecting the computed result, so at low concentrations the intensity of the radiation source and the gain of the detector are increased to allow the desired signal to be easily distinguished from noise. At higher concentrations, the radiation source intensity and detector gain are decreased in order to prevent saturation of the detector and the associated electronic circuitry.

Sensor Control Algorithms

Figure 5A:
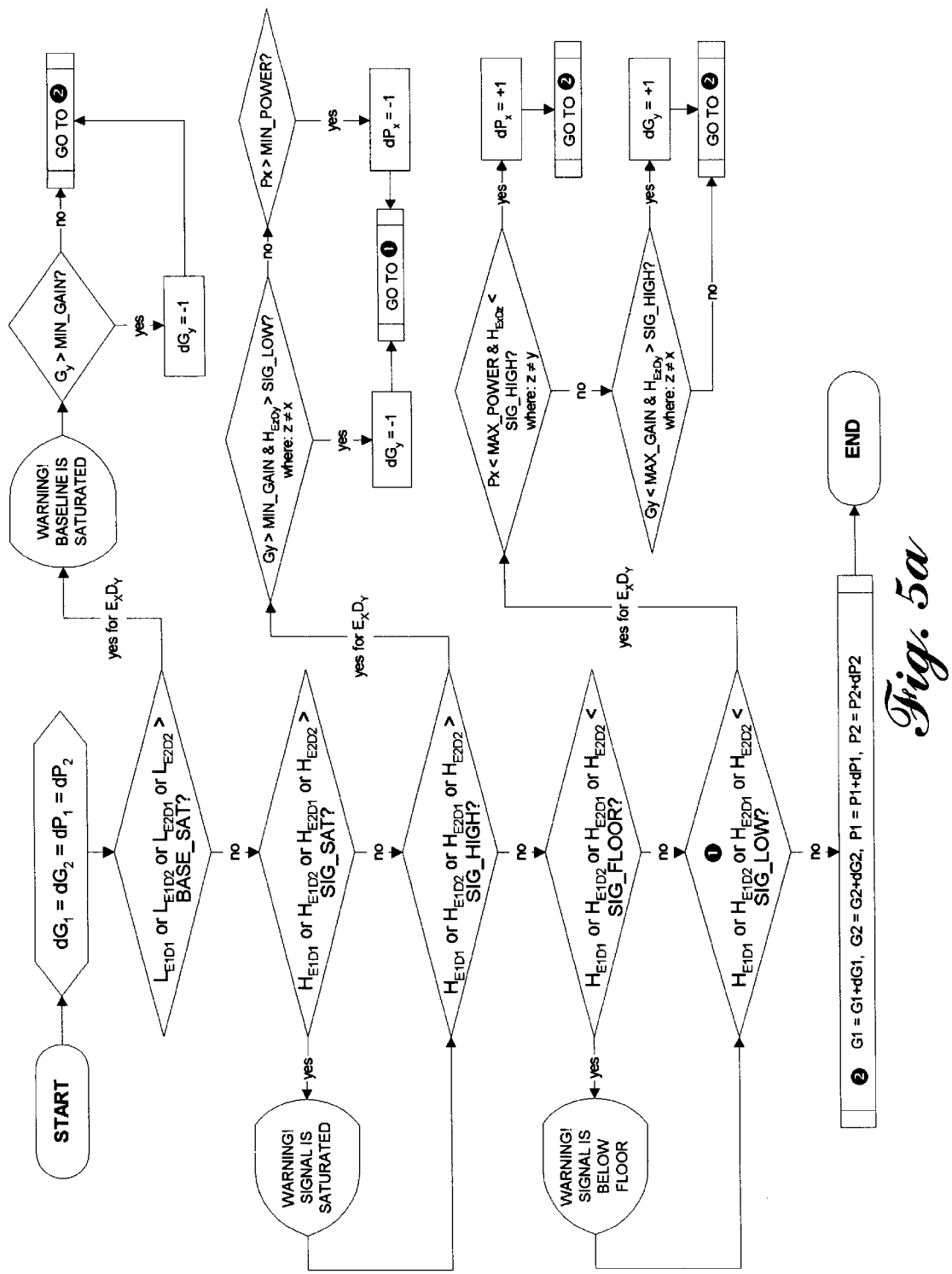
FIGS. 5a and 5b are flow charts summarizing the software code used by the sensor controller to set the source intensities and detector gain levels, and the measure the detector signals.

A flow chart describing the software embedded in the sensor controller 21 (FIG. 1) that dynamically controls the radiation source intensity (P) and detector gain (G) is shown in FIG. 5a. The algorithm specifies incremental changes to be made to the radiation source intensity (dP) and detector gain (dG). The general principal behind the algorithm is to keep the signal, H, generated by each radiation source and detector pair within a predetermined range (SIG_LOW<H<SIG_HIGH) while maintaining the radiation source intensity and detector gain within ranges where they are well-behaved (MIN_POW<P<MAX_POW and MIN_GAIN<G<MAX_GAIN). The algorithm is also designed to favor high radiation source intensity over high detector gain in order to maximize the signal to noise ratio of the measured signals. This aspect of the algorithm is particularly important for measuring low concentrations of cells or microorganisms. For the combined result in eq. 1 to be properly compensated, the signals must be linearly dependent on both source intensity and detector gain. If the signals are at risk of falling outside of the range of linear behavior (H>SIG_SAT), the user is warned by an indicator 22 on the sensor controller, and the algorithm takes steps to correct the situation. If the signal measured when the sources are off, L, is saturated (L>BASE_SAT), ambient radiation is assumed to be interfering with the measurement. The user is warned through an indicator 22 on the sensor controller, and the detector gain is decreased in an attempt to correct the saturation condition. The user may also be warned through an indicator on the sensor controller if any of the sensor signals falls below a predefined threshold (H<SIG_FLOOR). In the current embodiment, the algorithm is executed once every 125 ms after the signals have been measured and averaged 800 times. The algorithm will typically require multiple iterations before all signals fall within the desired range. In alternative embodiments of the present invention, only the source intensities, or only the detector gains, or neither, could be dynamically controlled.

Figure 4B:
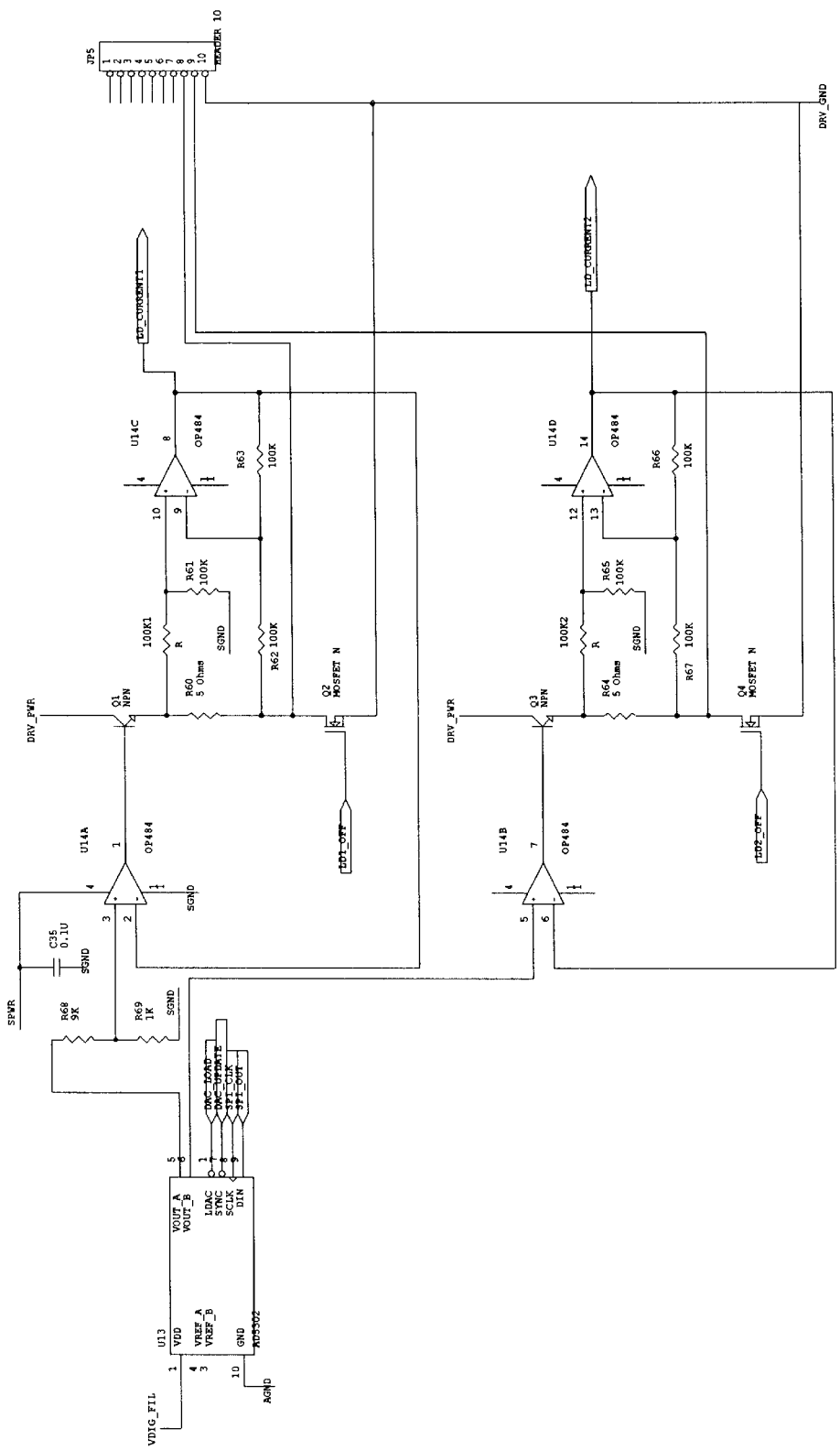
FIGS. 4b to 4e are schematics of the electronic circuits used in the sensor controller.
Figure 5B:
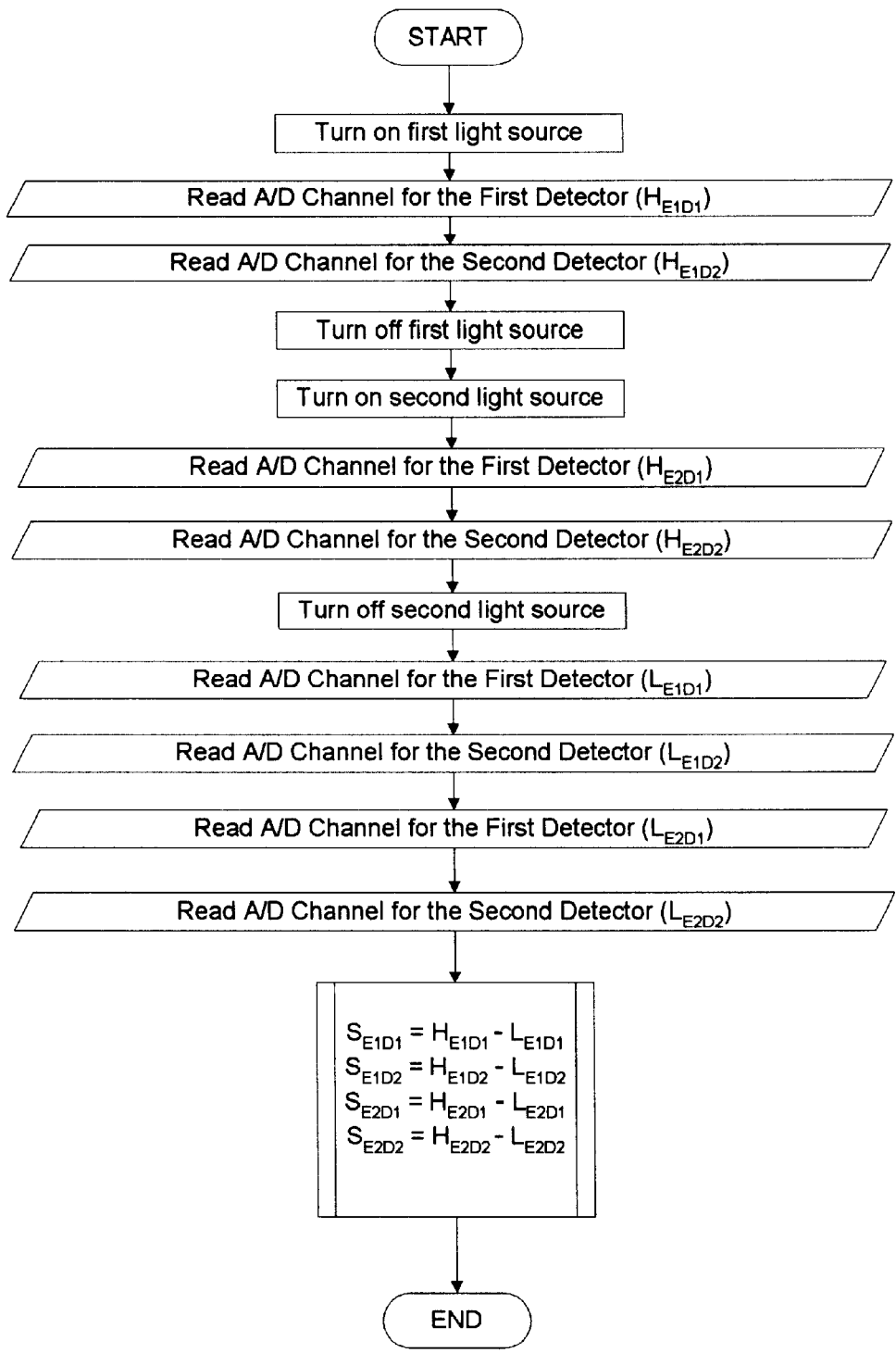

The presently preferred method of separately measuring the four signals from the two radiation sources and two detectors on the sensor is accomplished by alternately switching the two sources on and off and measuring the output of the detectors. The four signals are measured both when the sources are on, H, and off, L. The difference between H and L, S, is thus compensated for stray radiation that reaches the detectors. A flow chart describing the software embedded in the sensor controller that determines the method of measuring the four signals ($S_{E1D1}$, $S_{E2D1}$, $S_{E1D2}$, $S_{E2D2}$) is shown in FIG. 5b. In the present embodiment, one iteration of the algorithm outlined in FIG. 5b is performed in 125 $\mu$s. The algorithm is repeated so that the four signals are averaged 800 times before the sensor control algorithm (FIG. 5a) is repeated. The ordering of many of the steps in the algorithm diagrammed in FIG. 5b could be modified without substantially effecting the performance of the concentration measurement. The rate at which the signal conversion algorithm is repeated is set at a value that is convenient and reliable for the specific microcomputer (Motorolla MC68HC711E9CFN3) used in the present electronic circuit (FIG. 4b). Higher rates of signal conversion could be achieved through the use of a faster microprocessor and analog to digital converter.

In addition to averaging the 800 signals, digital filtering and/or outlier rejection may also be used to increase the signal to noise ratio of the signals. In the preferred embodiment, signals falling outside of upper and lower thresholds are rejected. The upper and lower thresholds are defined by computing the mean and standard deviation of the 800 signals and respectively adding and subtracting a multiple of the standard deviation from the mean. Alternatively, a histogram of signal voltages is computed and only those signals falling within a certain range of the median value are accepted. The range of values that are accepted may be determined from pre-set limits or on a percentage basis (e.g. Accept 90% of the values based on which values are closest to the median value). The result of this outlier rejection will be a reduction of the influence on the biomass determination of the effect of spurious electronic noise as well as radiation reflections due to such material as gas bubbles. Discrimination against radiation scattering from gas bubbles will be most effective at low concentrations of gas bubbles compared to biomass. For discrimination against the effect of gas bubbles at higher concentrations, additional methods are provided (see sections entitled "Additional Embodiments" and "Alternative Embodiments").

Alternative methods of separately detecting the individual signals from the two detectors and two radiation sources are also possible. In an alternative embodiment, the two radiation sources are continuously modulated with distinct temporal waveforms. The signals are jointly detected but then separated electronically or mathematically after digitization. These methods include modulating each radiation source at a distinct frequency, so that they can be separated using standard frequency demodulation techniques (also known as 'lock-in detection') or modulating the sources using 'spread spectrum' techniques such as direct-sequence spreading as is done in present cellular communication.

Electronic Circuits in the Preferred Embodiment—FIGS. 4a to 4e

Figure 4C:
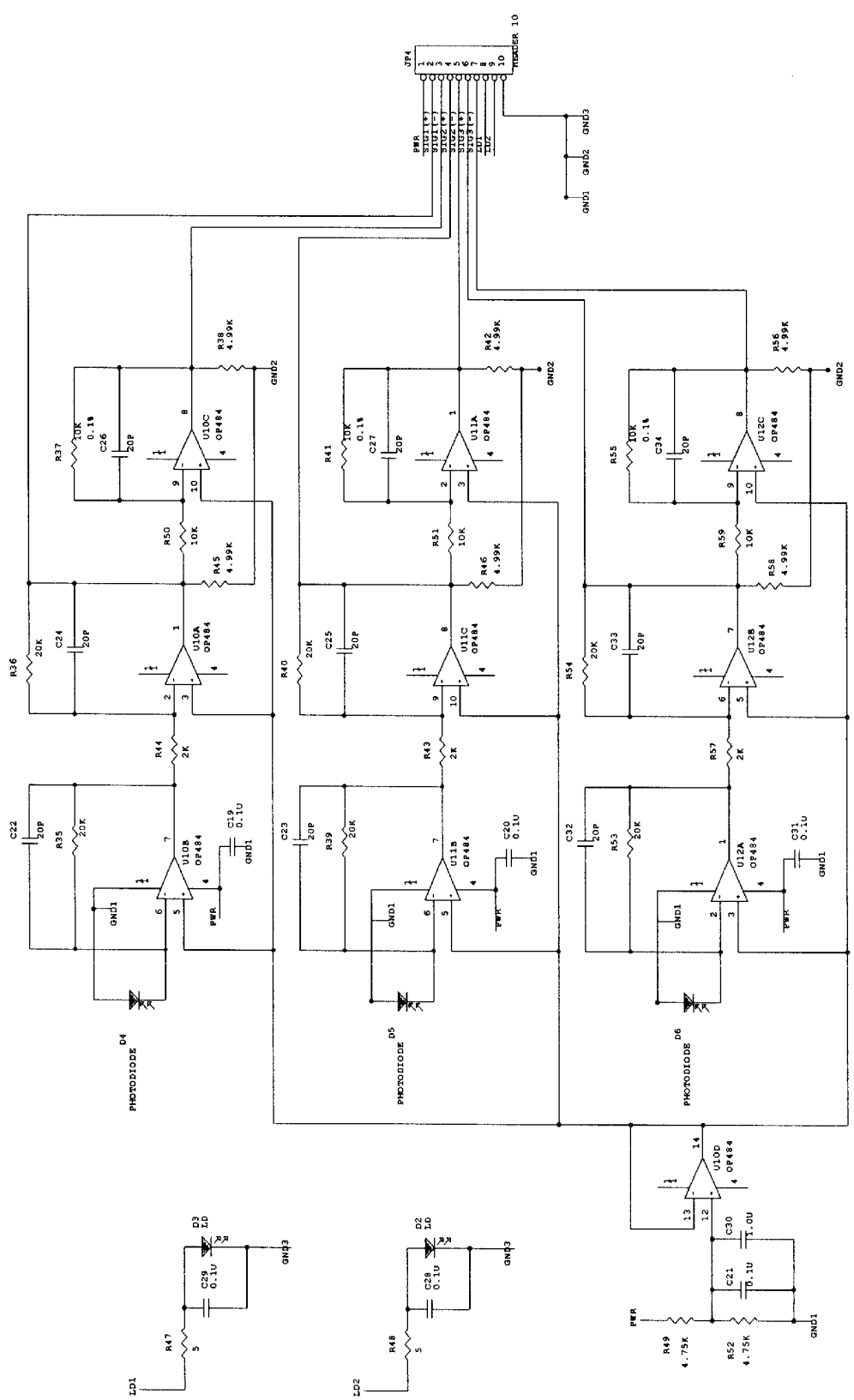

Within the sensor, each detector produces a current that is linearly proportional to the intensity of the detected radiation. The circuit diagram in FIG. 4a, shows how the current is converted to a voltage and then amplified in two stages. The amplified signal voltages are then carried through the sensor cable to the sensor controller. In the sensor controller, differential amplification is used to remove stray electronic noise that was picked up in the sensor cable (FIG. 4b). A digitally controlled potentiometer is used to control the gain of additional amplification of the signal voltages, which are then converted from analog to digital signals (FIG. 4c). The digital signal is then sent to a microprocessor (FIG. 4c). In the microprocessor, the digital signals from the two detectors are combined according to eq. 1. The combined result is then sent to the controller display. Alternatively, the combined result may be modified using a mathematical function (e.g. taking the logarithm of the combined result). As a further alternative, the combined result may be modified based on a previously determined calibration (see section below: "Calibration of the Sensor Result") to correspond to a parameter of interest (e.g. optical density or the concentration of the cells or microorganisms in the liquid culture). As yet another alternative or as a method of applying the calibration, the combined result may be used to index a lookup table to determine the number sent to the controller.

Figure 4D:
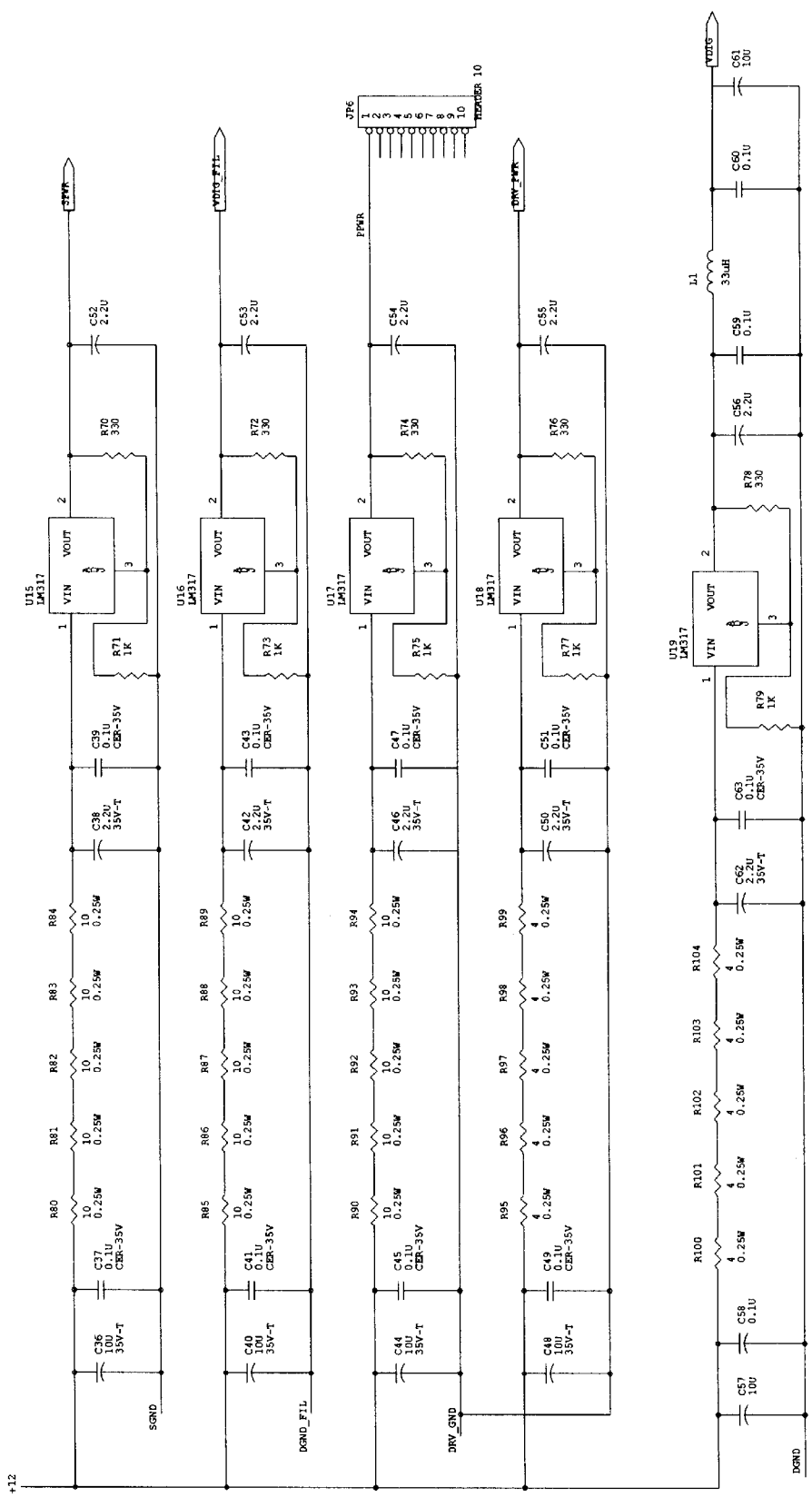
Figure 4E:
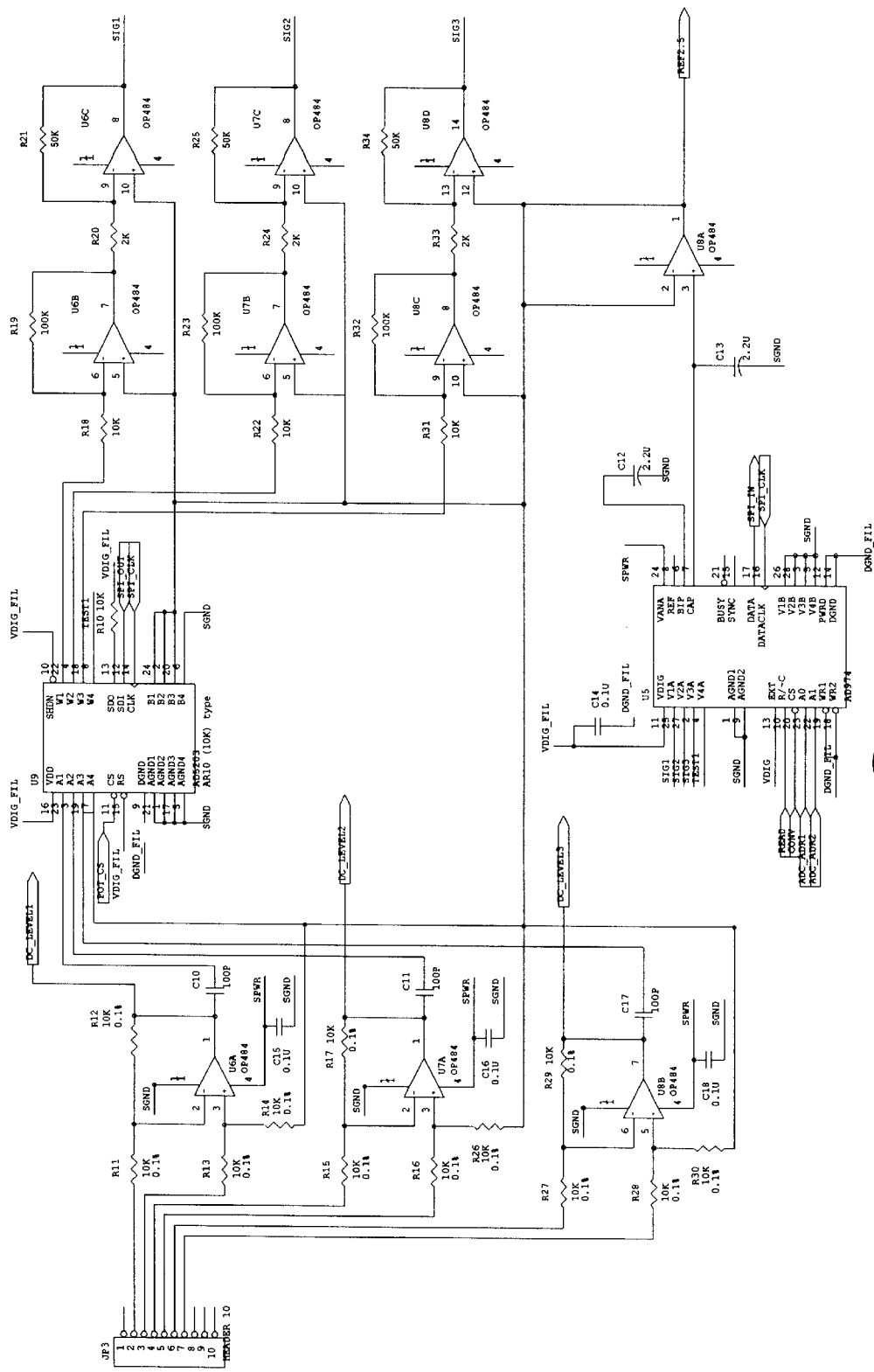

The microprocessor uses the algorithm diagrammed in FIG. 5a to set the detector gains through the digital potentiometer and to set the radiation source intensities. FIG. 4d shows the electronic circuitry used to control the radiation sources. The signal from the microprocessor, is converted from digital to analog, and then amplified to provide a current source for the VCSELs. The microprocessor (FIG. 4c) is also connected to an RS-232 controller, through which the amplified detector signals can be sent to a processor 25 (refer to FIG. 1) in digital form. The power supply diagrammed in FIG. 4e provides low-noise power to the circuits in the controller and sensor.

Discrimination Against Stray Radiation

Radiation that is not emitted by either of the radiation sources, but that is detected by the detectors, represents a potential source of interference ("stray or background radiation") with the measurement of the biomass in the liquid culture. The preferred embodiment of the present invention provides discrimination against stray radiation by subtracting the signal measured when both sources are off from the signals measured when the sources are on (see FIG. 5b). In an alternative embodiment, the radiation sources are continuously modulated and stray radiation is discriminated against by the use of appropriate demodulation or spread-spectrum techniques. If the stray radiation is modulated, the present invention will be most effective at discriminating against such radiation if the waveform of the sensor sources is most orthogonal to that from the background sources. For example, if the room lights are modulated at 60 Hz, it would not be advisable to turn on and off the radiation sources of the sensor at this frequency.

An extremely bright source of stray radiation, such as might be present in fermenters designed to produce photosynthetic cultures of cells or microorganisms, might cause saturation of one or both of the detectors on the sensor. In this case, the user is warned by an indicator on the controller, and the gain of the detectors is reduced. In an additional embodiment of the present invention, a radiation filter is placed in front of the detector. The radiation filter is chosen to pass radiation preferentially at the wavelengths emitted by the sensor sources compared to stray radiation. If the wavelength of the radiation sources specified in the preferred embodiment of the present invention (850 nm) is too close to a source of stray radiation, longer or shorter wavelengths may be used for the sensor sources.

Compensation for Window Thickness

The biomass is determined independently of the particular type of fermenter on which the measurement is made, by mounting the sensor a variable distance from the fermenter window. FIGS. 6a and 6b illustrate the effect that two different window thicknesses, T and T', have on a ray of light 62 emitted by a radiation source 29. The ray of light is emitted from the light source at an angle, $\theta_1$, relative to the axis normal to the sensor surface. When the light ray enters the glass window, it travels at a new angle, $\theta_2$, that is determined by the indices of refraction of the window material ($n_2$) and the medium between the radiation source and the window ($n_1$):

$$\frac{\sin\theta_1}{\sin\theta_2} = \frac{n_2}{n_1} \qquad (\text{eq. 4})$$

The displacement of the light beam from the radiation source in the direction parallel to the window surface 64 is $Y_1$ and $Y_2$, between the radiation source and window surface, and within the window, respectively. The total displacement, $Y_1+Y_2$, will determine the extent of overlap between the radiation emitted by the source into the liquid culture and the radiation emanating from the liquid culture that is captured by the detector. If the sensor is mounted the same distance, X, from a window with a different thickness, T', as shown in FIG. 6b, the displacement of the light beam will be the same ($Y_1$) in the space between the source and the window, but different within the window ($Y_2'$). The total displacement, $Y_1+Y_2'$, will be different, and the signal measured by the detector will be different. However, as shown in FIG. 6c, by changing the gap between the source and the window surface 64 to a new distance, X', the displacement of the light beam in the space between the source and the window surface can be modified to compensate for the effect of changing window thickness. A single setting for the distance between the source and the window surface can be used to compensate the displacement of all light rays to the extent that:

$$\frac{\tan\theta_1}{\tan\theta_2} \approx \frac{\sin\theta_1}{\sin\theta_2} \qquad (\text{eq. 5})$$

This relation only holds in the limit that $\theta_1$ and $\theta_2$ are small angles or $\theta_1$ and $\theta_2$ are very close in value.

In practice, these theoretical requirements can be satisfied by several alternative methods. In the preferred embodiment, air ($n_1=1$) fills the gap between the source and the window surface, and the window is made of crown glass ($n_2=1.5$). The distance, X', between the sensor and the surface of the window is chosen according to:

$$X' = \frac{n_1}{n_2}(T - T') + X \qquad (\text{eq. 6})$$

where T is the thickest window that the sensor is designed to accommodate, and T' is the window thickness of the fermenter actually being measured. The angles $\theta_1$ and $\theta_2$ are restricted to small values by using a well-collimated radiation source such as a VCSEL. The corresponding angles of the detected radiation can also be restricted to small values by using lensed detectors (e.g. Hamamatsu Photonics, part no. SMD-108). However, in the currently preferred embodiment the detectors are not lensed; the small area of the detectors and the distance between the liquid culture and the detectors being sufficient to limit the range of radiation ray angles that are detected.

In an alternative embodiment, the space between the sensor and the surface of the window is filled with a material whose index of refraction is a closer match to the window material than is air. If glass with the same index of refraction as the window material is used to fill the gap, the need to collimate the radiation sources and detectors is eliminated. Alternatively, an index-matching gel (such as Nyogel OCK-451 sold by Nye Lubricants Inc.) or like materials may be used to fill the space between the sensor and the window surface. In either of these cases, radiation sources with wider angular divergence, such as light-emitting diodes (LEDs), could be used in place of VCSELs.

It is also desirable to avoid specular reflection of the radiation sources from either the exterior or interior surface of the window onto the detectors. By considering the angular divergence of the radiation from the source and the thickness of the window, the minimum separation distance between radiation source and detector that avoids detection of specular radiation can be determined. The use of a well-collimated radiation source such as a VCSEL allows small separation distances to be employed in the sensor without interference due to specular reflection from the window. Small separation distances (<5 mm) are critical if high concentrations (>50 g/L) of cells or microorganisms are to be measured.

Extended Dynamic Range and Improved Linearity Compared to Prior Art

By using at least three unique separation distances between multiple radiation sources and multiple detectors, the present invention allows for measurement of biomass in liquid cultures over a wider range of concentrations and/or with improved linearity compared to prior art. This is demonstrated in FIGS. 9a to 9c using a liquid culture of Baker's yeast in water. The highest concentration of yeast was obtained by slowly mixing 908 grams of active dry yeast (Fleischmann's Yeast #2133, Burns Philp Food Inc.) with water to achieve a final volume of 4 liters. Lower concentrations of yeast were prepared by diluting this initial solution with water. A glass vessel with wall thickness of 11.2 mm was used to hold the yeast solutions. The sensors were mounted externally to the glass container with no gap between the sensor and the glass container. All sensors used the same components (see Description of Preferred Embodiment) but in different configurations. The electronic circuitry and software algorithms used to process the sensor signals were also identical. The gain of the detectors and the intensity of the radiation sources were held fixed during the measurements, to the extent possible, so that the prior-art sensor that is not compensated for changes in detector gain and source intensity (FIG. 9a) could be used with the same algorithm.

A sensor containing a single radiation source and a single detector, at a separation distance, d, as provided in prior art, U.S. Pat. No. 5,483,080, is shown on the left in FIG. 9a. The graph on the right in FIG. 9a shows the signal from the sensor as a function of concentration for three configurations corresponding to three separation distances (d=3.1 mm, 9.4 mm, and 15.8 mm). From the figure one can see that by changing d, it is possible to change the range of over which the sensor has maximum sensitivity to changes in concentration of yeast. When d is large (d=15.8 mm), the sensor has greatest sensitivity to changes in concentration when the yeast concentration is low (0.5–5 g/L). By decreasing d, the range of sensitivity is shifted to higher concentrations. For example, when d is 3.1 mm, the sensor has maximal sensitivity to changes in yeast concentration over the range of approximately 5 to 50 g/L. By using only a single separation distance in the sensor, this technique provides a limited range over which the concentration of yeast can be accurately determined. Further, the sensor response is highly non-linear with respect to changes in yeast concentration. Additionally, the accuracy of the technique is limited by the fact that the sensor response is not compensated for changes in source intensity or changes in the optical coupling efficiency between the sensor and the liquid culture.

A compensated sensor configuration provided in prior art, European Patent Application EP0945100A1, is shown on the left in FIG. 9b. This configuration is constrained to have only two unique separation distances, $d_1$ and $d_1+d_2$, between the two radiation sources and two detectors. The graph on the right side of FIG. 9b shows the result of combining the four sensor signals as provided by eq. 1. The results for three configurations, differing in the distances $d_1$ and $d_2$, are shown overlaid on the graph. Whether $d_1$ is larger ($d_1$=9.4 mm, $d_2$=3.2 mm), equal ($d_1$=$d_2$=3.1 mm), or smaller ($d_1$=3.1 mm, $d_2$=6.3 mm) than $d_2$, the combined response, R, is not linear, nor even monotonic over a wide range of yeast concentrations. Thus, even though the sensor is compensated for source intensity, detector gain, and optical coupling efficiency, the sensor is not suitable for determining the biomass in liquid cultures over a wide range of concentrations.

The compensated sensor provided by the present invention is shown on the left side of FIG. 9c (also shown in FIG. 3a). The sensor is arranged such that there are four separation distances, $d_1$, $d_2$, $d_3$, and $d_4$, between the two radiation sources and the two detectors, at least three of which are unique (in the currently preferred embodiment three are unique: $d_1$=6.3 mm, $d_2$=9.4 mm, $d_3$=3.1 mm, $d_4$=9.4 mm). As shown on the right side of FIG. 9c, combining the four sensor signals according to eq. 1 produces a combined result, R, that has both a wider range of sensitivity and a more linear response to changes in concentration compared to the prior art (FIGS. 9a and 9b). Notice that the linear response behavior of the present invention is observed on a log-log scale (FIG. 9c). Thus by computing the logarithm of R, the sensor result will be linear with the log of concentration. Since cells or microorganisms in a fermenter typically grow exponentially during a substantial portion of their growth cycle, the output result of the present invention provides an inherent advantage: exponential growth over several orders of magnitude of concentration can be accurately measured with the same sensor and the logarithm of the un-calibrated output will be linear with respect to time.

Calibration of the Sensor Result

The combined result from eq. 1, R or log(R), may be used directly as an indication of the biomass in a cell culture. Alternatively, it may be desirable to convert R into more standard units such as optical density per centimeter, number of cells or microorganisms per liter, or grams of cells or microorganisms per liter. For this purpose, a calibration can be generated that is used to convert R into the desired units, B. The calibration curve consists of a mathematical function, $f(R)$, that relates the value R to B. The calibration curve is generated by measuring the combined result from eq. 1, R, throughout an actual fermentation run (or runs) and simultaneously measuring the concentration, B, by a standard reference method. For example, if the desired units are optical density, small portions of the liquid culture are extracted during the fermentation run, the portions are diluted to have an optical density between approximately 0.2 and 1.0, and the optical density is multiplied by the dilution factor. As a second example, if the desired units are grams of dry-weight cells or microorganisms per liter, defined volumes of the liquid culture are extracted throughout the fermentation run, the volumes are dried, weighed, and the dry weight is divided by the volume that was extracted. The term "fermentation run" is used here to mean the cycle in which an inoculant of cells or microorganisms is first added to the liquid medium until the time at which the biomass is harvested.

If the relationship between R and B at all points in the fermentation run can be represented by a simple mathematical function, $f(R)$, the parameters of $f$ can determined by a least squares fit of $f(R)$ to B. For example, in FIG. 9c, the relationship between log(R) and log(C) (where C is dry weight of yeast per liter of liquid culture) is nearly linear. A calibration can be established by determining the values of a and b in the relationship $f(R)=a\log(R)+b$ that minimize the sum of the squares of the difference between $f(R)$ and log(C) for all measured data points. Alternatively, if all points in the fermentation run cannot be represented by a simple mathematical function, a series of simple mathematical functions determined by interpolating between adjacent experimentally measured data points can be used in the calibration. For example, referring again to FIG. 9c, measurements at the highest and lowest concentration values show deviation from linear behavior. A more accurate calibration in these regions may be obtained by interpolating between adjacent points in the graph. The choice of which calibration function to be used is then determined by the range of values of the currently measured value of R.

The calibration will provide the most accurate predictions of concentration if generated on the same fermenter, growing the same cells or microorganisms, under the same growth conditions as the fermentation currently being predicted. However, a more universal calibration may provide adequate measurement accuracy, because the present invention provides several means for making the calibration have reduced sensitivity to the particular fermenter, the conditions under which the fermenter is operated, and the particular sensor that is used to perform the measurements. The self-compensating features of the present invention have the effect that it is unnecessary to compensate for sensor-to-sensor differences in detector sensitivity or radiation source intensity. Fermenter-to-fermenter differences in the properties of the window through which the sensor injects and detects radiation are also compensated. By the use of variable spacing between the sensor and the fermenter window (see above: "Compensation for Window Thickness") the effect of variable window thickness is also compensated. Accumulation of material on the surface of the window during the course of a fermentation run is also compensated by the present invention.

User Interface to the Sensor Controller

In the preferred embodiment of the present invention, the controller provides an alphanumeric display 23 (FIG. 1), that displays a quantity related to the biomass in the cell culture. In addition, indicators are used to alert the user to the status of the sensor. Status indication could be one of the functions of the alphanumeric display, or separate indicators could be used, or both. In the preferred embodiment, both the alphanumeric display 23 and separate LED indicators 22 are used to alert the operator to the following conditions:

i) background radiation alone saturates one or more detector (baseline is saturated), ii) signal causes detector saturation, iii) signal is so small that detector is below 'floor' level, iv) sensor is operating normally.

The user is also provided a means of affecting the operation of the controller through controller buttons 24 (FIG. 1). The controller buttons may be used at the beginning of a fermentation run, allowing the user to set a baseline from which increases in the combined result are to be reported to the alphanumeric display. The controller buttons may also be used to allow the user to place data in the electronic record of the fermentation to indicate, for example, the time at which an inoculant was injected into the growth medium. The controller buttons may also be used to obtain data such as the serial number or date of manufacture of the controller itself In an alternative embodiment of the present invention, the controller is housed on a board that resides in a processor 25. In this embodiment, the controller contains no user interfacing components. User interface is accomplished through the processor. Power for the controller can be supplied through the processor and the need for a sensor controller cable 46 is eliminated.

Operation of the Processor

Although the controller can be operated independently as a concentration monitor, in the preferred embodiment of the present invention, the controller is connected by a sensor controller cable 46 to a processor 25. The processor can be used to perform any of the following functions:

(1) Display the concentration measurements as a function of time.

(2) Display the rate of change of concentration.

(3) Remotely operate the sensor controller.

(4) Collect calibration data from a fermentation run.

(5) Use calibration data to convert the combined result, R, from eq. 1 into more standard units such as optical density per centimeter, number cells or microorganisms per liter, or grams of cells or microorganisms per liter (6) Alert the user to various events related to the sensor such as:

i. Baseline is saturated.

ii. Signal is saturated.

iii. Signal is below floor.

(7) Alert the user to various events related to the fermentation such as:

i. Time for induction ii. Time to harvest cells iii. Need to change settings of the fermenter controller (8) Provide a feedback signal for the fermenter controller (see below). In addition to the functions listed above, the processor may be user-configurable so that the user is able to add other functions of interest.

Feedback Control of Fermentation

While the present invention can be simply used to passively monitor the biomass in a liquid culture, the preferred embodiment includes a means of actively providing feedback to a fermentation controller 27 (FIG. 1). The optimum conditions for growth of cells or microorganisms in a liquid culture will change during the growth cycle. For example, as the biomass increases, the rate of oxygen and nutrient consumption in the fermenter may increase. The present invention provides a method and device for continuously measuring the biomass in a liquid culture. The measured concentration can be converted by the processor into a feedback signal that is sent to the fermentation controller and used to control the settings of such parameters as dissolved oxygen, rate of stirring, and nutrient feed rate. Through the method(s) and device(s) provided by the present invention, the operator can easily run experiments to identify optimal growth conditions for particular organisms. Once identified, the present invention can then be used to reproducibly implement the optimal growth conditions in subsequent fermentation runs.

In addition to providing optimal growth conditions, the present invention can be used to identify the optimal time in the growth cycle for induction of chemical production. By providing both the absolute biomass and the rate of change of concentration, the optimal induction point will be readily identifiable from one fermentation run to the next. This will have the effect of increasing the yield of chemical product that is ultimately isolated from the liquid culture. The optimal harvesting time may also be more readily identifiable using the present invention.

ALTERNATIVE EMBODIMENTS

Fiber Optic Sensor

Fiber optic means may be used to remotely locate the emitters and detectors from the fermenter itself In this embodiment, the emitters and detectors are housed within the controller unit, preferably on the same circuit board that contains the electronic means to operate them. The emitters and detectors are then each separately optically coupled to suitable optical fibers. The fibers would be contained in a cable which runs from the controller to the sensor. The optical fibers are themselves either mounted to an attachment plate which is placed on the exterior of the fermenter or mounted in an immersion probe, with both mounting methods allowing radiation to be emitted and detected in an equivalent way to the preferred embodiment described infra.

Alternate Methods of Externally Mounting the Sensor

Many alternate means can be envisioned to mount the sensor to the outside of the fermenter. An adjustable elastic strap could be provided to surround the circumference of the typically cylindrical fermenter, the sensor then being coupled to the attachment plate which is itself coupled to the elastic strap. The elastic strap would provide sufficient force normal to the surface of the fermenter to more than support the weight of the attachment plate and sensor. Alternatively, many fermenters have a set of externally arranged, vertically disposed proximal metal rods that serve to attach metal plates to the top and bottom of the otherwise open-ended cylindrical glass vessel. In alternative embodiment of the present invention, a common rod clamp is used to mount the sensor to such a rod with a simple articulated clamping arm.

Immersible Probe

Figure 10A:
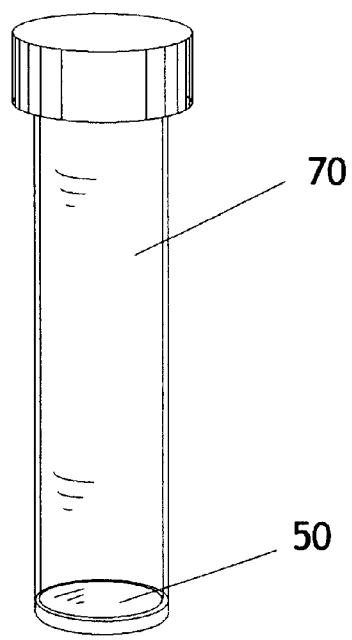
FIGS. 10a and 10b show sensor housings to be used when a radiation sensor is immersed in a liquid culture to measure biomass.
Figure 10B:
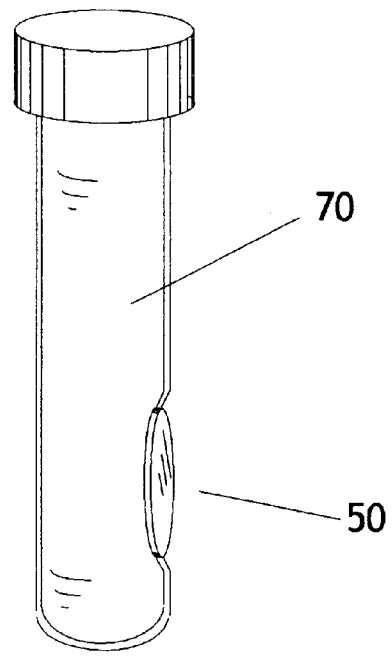

In addition to the preferred embodiment, which provides a method and device for measuring the biomass through an external window of a fermenter, an alternative embodiment of the present invention provides a sensor that is immersed in the liquid culture. The internally mounted embodiment has the advantage that variable window thickness from fermenter to fermenter does not need to be compensated. A housing provides protection to the sensor against the environment within the fermenter (including sterilization). FIGS. 10a and 10b show two embodiments of a housing 70 used to hold the immersible probe. The housing in FIG. 10a provides a window 50 into the liquid culture through the bottom of the housing, whereas FIG. 10b provides a window 50 through the side of the housing. In either case, the sensor mounted behind the window are of similar design (FIGS. 3a to 3e) to those used for an externally mounted measurement.

Sensor Employing Sample Withdrawal

The sensor of the present invention may also be used to monitor samples of the liquid culture that are withdrawn at intervals from the fermenter. By providing a means to withdraw the liquid, employ the radiation detection method described in the present invention, and optionally return the liquid to the fermenter, automated measurement can thereby be accomplished.

Alternative Methods of Combining the Sensor Signals

The specific method of combining the sensor signals described by eq. 1 is but one of many possible methods. For example, the four signals supplied by the sensor could be combined as a weighted linear sum of logarithms:

$$R = a \cdot \log(S_{E1D1}) + b \cdot \log(S_{E2D2}) + c \cdot \log(S_{E1D2}) + d \cdot \log(S_{E2D1}) \quad \text{(eq.7)}$$

where a, b, c, and d are weighting terms. Notice that by setting a, b, c, and d to 1, 1, −1, and −1, respectively, eq. 7 is reduced to the logarithm of eq. 1a. In an alternative embodiment of the present invention, the weighting terms are chosen to maximize the range of sensitivity of the combined result, R, to changes in concentration. In another embodiment of the present invention, the weighting terms are chosen to maximize the linearity of the combined result to changes in concentration. In yet another embodiment of the present invention, the weighting terms are chosen to minimize the effect of interferences on the concentration measurement. The types of interferences that could be minimized includes: (a) changes in radiation source intensity, (b) changes in detector gain, (c) changes in radiation coupling efficiency between the sensor and the liquid culture, (d) gas bubbles in the liquid culture, (e) reflective objects in the fermenter, (f) variable window thickness, and (g) variable stirring rates.

ADDITIONAL EMBODIMENTS

FIGS. 3b and 3c—Sensor With More Than Two Radiation Sources and Two Detectors

Additional embodiments of the sensor of the present invention, illustrated in FIGS. 3b and 3c, have additional radiation sources and/or detectors beyond the two radiation sources and two detectors specified in the preferred embodiment (FIG. 3a). The additional signals provided by these additional components can be used to compute additional combined results, R, from either eqs. 1 or 7. For example, with the sensor embodiment illustrated in FIG. 3b, three combined results can be obtained using eq. 1a:

$$R_1 = \frac{S_{E1D1}S_{E2D2}}{S_{E1D2}S_{E2D1}} \quad R_2 = \frac{S_{E3D1}S_{E2D2}}{S_{E3D2}S_{E2D1}} \quad R_3 = \frac{S_{E1D1}S_{E3D2}}{S_{E1D2}S_{E3D1}} \quad \text{(eq. 8)}$$

The additional information provided by the two additional combined results, $R_2$ and $R_3$, allows for further compensation of potential sources of interference to the measurement of biomass. For example, optimal growth of many types of cells or microorganisms requires that gas be mixed with the culture. However, gas bubbles suspended in the liquid can scatter radiation and lead to a detected signal that may be falsely interpreted as due to scattering from cells or microorganisms. The diameter of gas bubbles are typically much greater than that of cells or microorganisms and have a different index of refraction. As a result, gas bubbles scatter radiation with a different intensity and angular distribution than do cells or microorganisms. If the radiation scattering by gas bubbles is an infrequent event compared to scattering by cells or microorganisms, signal processing means may provide adequate discrimination against gas bubbles (see earlier section: "Sensor Control Algorithms"). However, at high concentrations of gas bubbles, the signal processing may not provide adequate discrimination.

In such cases, the alternative embodiment illustrated in FIG. 3b may be used. The three combined results, $R_1$ to $R_3$, are computed from three sets of radiation sources and detectors that have three unique geometrical arrangements. Consequently, each combined result, R, provides unique information about the angular distribution of radiation being collected. By combining $R_1$, $R_2$, and $R_3$ the concentration of gas bubbles can be separated from the concentration of suspended cells or microorganisms. Similarly, large objects inside the liquid culture vessel that reflect radiation in a specular fashion, will do so with a very different angular distribution than cells or microorganisms suspended in the liquid culture. Such objects might include a pH probe or stirring apparatus. The additional combined results, $R_2$ and $R_3$, can again be combined with $R_1$ to separate the effect of scattering due to cells or microorganisms from the effect of specularly reflecting objects in the vessel.

The mathematical equation used to combine $R_1$, $R_2$, and $R_3$ may be derived from the theoretical angular distribution of the sources of interference compared with that of the suspended cells or microorganisms whose concentration are to be measured. For example, given the size of the scattered object, the wavelength of the radiation, the index of refraction of the object and its surrounding medium, Mie theory can be used to predict the angular distribution of scattered radiation (see for example, "Light Scattering by Small Particles" by H. C. van de Hulst, Dover Publications, New York, 1981). By comparing the angular distribution predicted for gas bubbles with that of the suspended cells or microorganisms, the contributions to $R_1$, $R_2$, and $R_3$ by each species may be determined. A mathematical relationship may then be derived to separately determine the biomass based on $R_1$, $R_2$, and $R_3$.

Alternatively, the mathematical relationship between $R_1$, $R_2$, and $R_3$ may be determined empirically as part of the calibration of the sensor. Referring back the section entitled "Calibration of the Sensor Result", part of the calibration may include varying such parameters as rate of bubbling and rate of stirring so that the effects of these variations may be determined and compensated. The calibration equation then specifies that relationship between $R_1$, $R_2$, and $R_3$ that allows the biomass to be separated from interfering sources of radiation scattering. Methods of minimizing prediction errors based on multivariate models are well known in the art (see for example, "Multivariate Calibration" by Martens & Naes, Wiley, N.Y., 1989).

In addition to allowing the scattering from cells or microorganisms to be separated from interfering sources of radiation scattering, the angular information provided by multiple combined results allows the size distribution of the cells or microorganisms to be estimated. The size distribution of microorganisms is of particular interest for filamentous microorganisms whose size may vary considerably during a fermentation run. For this purpose, it may be useful to increase the number of radiation sources and detectors in the sensor yet further. The sensor illustrated in FIG. 3c includes three radiation sources (29, 30, and 32) and three detectors (40, 42, and 44). Using eq. 1 or eq. 7, nine unique combined results, R, can be computed. In a similar manner to the method by which the biomass is compensated for the effect of bubbles, the angular scattering distribution information provided by the multiple combined results, can modeled either theoretically or empirically to determine the size distribution in addition to the concentration of the cells or microorganisms.

The number of radiation sources and detectors may be further increased to improve the resolution and accuracy of the size distribution determination and/or the compensation for scattering objects other than cells or microorganisms in the liquid culture vessel.

FIGS. 3d and 3e—Use of Radiation Sources Emitting at Additional Wavelengths

In the preferred embodiment of the sensor of the present invention, illustrated in FIG. 3a, the wavelength of the radiation emitted by the two radiation sources is substantially equal. Alternative embodiments of the present invention include radiation sources that emit at wavelengths that are substantially different, two examples of which are illustrated in FIGS. 3d and 3e. In the sensor illustrated in FIG. 3d, radiation sources 29 (E1) and 30 (E2) emit radiation at substantially equal wavelengths. Radiation sources 32 (E3) and 34 (E4) also emit radiation at wavelengths that are substantially equal to each other, but different from radiation sources 29 and 30. The separation distances between radiation sources 29 and 30 and detectors 40 (D1) and 42 (D2) are substantially equal to the separation distances between radiation sources 32 and 34 and detectors 40 and 42. Therefore, except for differences due to the emission wavelength of the radiation sources, the combined responses, $R_1$ and $R_2$, defined in eqs. 9a and 9b, should be equal:

$$R_1 = \frac{S_{E1D1}S_{E2D2}}{S_{E1dD2}S_{E2D1}} \quad \text{(eq. 9a)}$$

$$R_2 = \frac{S_{E3D1}S_{E4D2}}{S_{E3D2}S_{E4D1}} \quad \text{(eq. 9b)}$$

Differences between $R_1$ and $R_2$, caused by the different emission wavelengths of the radiation sources, could include differences in radiation absorption and/or scattering. Specifically, in the case of radiation absorption, the preferred embodiment of the present invention utilizes radiation source emission wavelengths that specifically avoid the effects of substantial absorption of radiation by the liquid culture medium, the suspended cells or microorganisms, or the window of the vessel. For example, at the 850 nm emission wavelength of the VCSELs used in the preferred embodiment of the present invention, aqueous media, glass, and cells or microorganisms typically have very weak optical absorption coefficients ($<0.1$ cm$^{-1}$). As a result, the signals measured by the sensor will depend most strongly on the scattering properties of the liquid culture and only weakly on the absorption properties of the window or the liquid culture.

However, in certain situations of interest to users of the present invention, the above assumptions of weak absorption may not be valid. For example, the liquid culture may contain a photosynthetic organism having pigment molecules that absorb radiation substantially at the emission wavelength of the radiation source. In this case, the two combined results, $R_1$ and $R_2$, provided by the sensor shown in FIG. 3d may be used to discriminate between the effects of absorption and scattering by the cells or microorganisms. For example, if the two wavelengths of emission employed by the radiation sources are chosen so that the scattering coefficient is substantially the same at the two wavelengths but the absorption coefficient is substantially different, the two combined results $R_1$ and $R_2$ can be used to determine the differential absorption of the cells or microorganisms at the two wavelengths. The differential absorption measurement may be useful either as an independent method of estimating the biomass, or as a method of correcting the signal due to scattering for the effect of absorption.

A second example in which the assumption of weak absorption will not hold is if the wavelength of the radiation sources is chosen to correspond to a region of strong radiation absorption by a component of the medium. Water, although nearly transparent at visible light wavelengths and up to 900 nm in the near-infrared, absorbs radiation in a series of increasingly strong absorption bands peaking near 980 nm, 1180 nm, 1440 nm, and 1920 nm, respectively. Above 2500 nm, the penetration depth (defined here as the depth at which 90% of the radiation has been absorbed) of water is less than 100 $\mu$m. In the preferred embodiment of the present invention, these water bands are specifically avoided. However, in an alternative embodiment of the present invention, such as that which may be accomplished using the sensor illustrated in FIG. 3d, the two radiation source wavelengths are chosen so that one radiation source falls within a water band and the other radiation source is outside of the water band. The differential absorption by water at the two wavelengths may then be used as a method of absolute calibration of the path length traversed by the radiation beams. This path length may then be related to the biomass suspended in the liquid culture. The differential absorption measurement may also be used to determine the concentration of an analyte in the medium.

An additional use of the alternative embodiment illustrated in FIG. 3d is to compensate the measured biomass for the effects of radiation scattering by gas bubbles. Due to the differences in size and physical properties of bubbles and cells or microorganisms (see above section "Sensor with more than two radiation sources and two detectors"), the relative intensity of scattering as a function of wavelength is different for the two particle types. By measuring two combined responses, $R_1$ and $R_2$ (see eq. 9), from sensor configurations (FIG. 3d) that are identical except for the wavelength of the radiation sources, the biomass and concentration of gas bubbles can be separately determined. As described above ("Sensor with more than two radiation sources and two detectors"), the mathematical relationship used to convert $R_1$ and $R_2$ into the two concentrations can be derived theoretically or determined empirically through calibration. In one embodiment of the present invention, two types of radiation sources are employed: one that emits light in the visible to near infrared wavelength region, and a second that emits radiation in the millimeter to microwave region of the electromagnetic spectrum. By choosing one source wavelength that is on the same scale as the diameter of microorganisms (or their internal organelles) in the liquid culture and a second source wavelength that is on the same scale as the bubble diameter, the scattering contributions of these two distinctly different particles can be separated.

The number of radiation sources and detectors in the sensor may be further increased to gain further discrimination against sources of interference with the concentration measurement and/or to add the capability to determine the size distribution of cells or microorganisms in the liquid culture. For example, the embodiment illustrated in FIG. 3e combines the advantages of a sensor that provides measurements at multiple scattering angles (FIG. 3b) with a sensor that provides measurements at multiple radiation source wavelengths (FIG. 3d). In the sensor illustrated in FIG. 3e, radiation sources 29, 30, and 32 emit radiation at substantially equal wavelengths. Radiation sources 34, 35, and 38 also emit radiation at wavelengths that are substantially equal to each other, but different from radiation sources 29, 30, and 32. The separation distances between radiation sources 29, 30, and 32 and detectors 40 and 42 are substantially equal to the respective separation distances between radiation sources 34, 36, and 38 and detectors 40 and 42. By resolving the scattered radiation as a function of both angle and wavelength it is possible to make highly accurate measurements of the concentration and/or size distribution of cells or microorganisms, despite interferences from gas bubbles and reflecting objects suspended in the liquid culture.

It will be readily apparent to those skilled in the art, that many further embodiments of the present invention may be made by extension of those embodiments illustrated in FIGS. 3a to 3e.

Conclusion, Ramifications, and Scope

Accordingly, the sensor of this invention can be used to measure properties of materials over a wide dynamic range without the need for moving parts while having low sensitivity to such factors as radiation source intensity, detector gain, and radiation coupling efficiency between the sensor and material. In the specific application of this invention to the measurement of particle concentration in scattering media, the sensor output provides a wider dynamic range and a more linear response to changes in the logarithm of particle concentration than do sensors described in prior art, and the output is compensated for the accumulation of particles at the interface between the sensor and the scattering medium. The limited dynamic range of the sensors described in the prior art is a profound disadvantage when monitoring the typical course of a fermentation in which particle concentrations and their attendant optical properties may change by many orders of magnitude. Further, this invention provides means of discriminating between different particle types and/or measuring particle size distributions in addition to particle concentration. In the specific application of this invention to the measurement of biomass in liquid cultures, a means of monitoring the culture without the need to immerse the sensor in the liquid culture is provided. This reduces the necessary cost and complexity of the sensor housing and reduces the risk of contaminating the cell culture with foreign matter. A means of compensating the measured sensor response for the window thickness of the cell culture container is also provided.

Although the description above contains many specificities, these should not be construed as limiting the scope of the invention but as merely providing illustrations of some of the presently preferred embodiments of this invention.

Thus the scope of the invention should be determined by the appended claims and their legal equivalents, rather than by the examples given above.

What is claimed:

1. A method of determining at least one parameter of a medium which comprises the steps of:
    a) passing electromagnetic or acoustic radiation originating from each of a plurality of sources through said medium to a plurality of detectors;
    b) measuring a plurality of signals corresponding to the portion of radiation detected by each of said detectors that originated from each of said sources;
    c) selecting signals from a group consisting of all of said signals, and combining the selected signals in a manner that substantially reduces the sensitivity of the combined result to all of the following factors as compared to said signals considered separately:
    intensity of said sources,
    sensitivity of said detectors,
    coupling efficiency of radiation from said sources into said medium, and
    coupling efficiency of said radiation from said medium to said detectors;
        wherein said selected signals comprise the signals collected from a plurality of said detectors, each detecting radiation that originated from a plurality of said sources, the separations between said sources and said detectors including at least three unique distances; and
        wherein the selection of signals and said combining of the selected signals is carried out at least once whereby at least one said combined result is produced; and
    d) relating at least one of said combined results to at least one parameter of the medium.

2. The method of claim 1 wherein said radiation sources are each substantially monochromatic.

3. The method of claim 2 wherein said plurality of sources emit radiation of substantially identical wavelength.

4. The method of claim 1 wherein said sources and said detectors are arranged such that substantially only scattered radiation is detected by said detectors.

5. The method of claim 1 wherein at least one of said combined results is determined from the following equation:

$$\log\left(\frac{S_{E1D1} S_{E2D2}}{S_{E1D2} S_{E2D1}}\right)$$

where:
    E1 and E2 are a pair of sources from among said plurality of sources, and D1 and D2 are a pair of detectors from among said plurality of detectors;
    $S_{E1D1}$ is proportional to the intensity of radiation from source E1 that is detected at detector D1;
    $S_{E1D2}$ is proportional to the intensity of radiation from source E1 that is detected at detector D2;

$S_{E2D1}$ is proportional to the intensity of radiation from source E2 that is detected at detector D1; and $S_{E2D2}$ is proportional to the intensity of radiation from source E2 that is detected at detector D2.

6. The method of claim 1 wherein said at least one parameter being determined is related to at least one of: the concentration of at least one type of particle suspended in said medium, the average size of particles suspended in said medium, the size distribution of particles suspended in said medium, the chemical composition of particles suspended in said medium, the shape of particles suspended in said medium, and the chemical composition of said medium.

7. The method of claim 6 wherein said medium is a liquid culture containing a suspension of cells or microorganisms.

8. The method of claim 7, further including:
   a) varying the conditions of said liquid culture, including any combination of the concentration, size, and type of cells or microorganisms, the density, size, and type of gas bubbles, and the rate of stirring;
   b) establishing a calibration whereby for the range of said varied conditions, said combined results are related to known values of said at least one parameter of the medium; and
   c) utilizing said calibration to arrive at a determination of present said at least one parameter within said liquid culture from said combined results.

9. The method of claim 8 wherein one of said parameters being determined is the biomass suspended in said liquid culture.

10. The method of claim 9 wherein a means is provided to compensate the measurement of biomass for the effect of reflecting objects within the liquid culture other than cells or microorganisms.

11. The method of claim 7 wherein at least one of the parameters is used to control at least one process variable that affects the growth of said cells or microorganisms.

12. The method of claim 1 wherein the accuracy of said parameter determination is improved by at least one of:
   a) influencing the intensity of radiation emitted from at least one of said sources to bring at least one of said signals within some optimum range;
   b) influencing the amplification of the signal collected from at least one of said detectors to bring at least one of said signals within some optimum range.

13. The method of claim 1 wherein step (a.) is accomplished by immersing a probe within said medium.

14. The method of claim 1 wherein step (a.) is accomplished by mounting a probe externally to a container that holds said medium, said container providing a window into said medium that is substantially transparent to the radiation emitted by said sources.

15. The method of claim 14 wherein the influence of the thickness of said window on the determined value of said parameters is reduced by including at least one of the following:
   a) at least one source which emits substantially collimated radiation,
   b) substantial collimation of the radiation emitted by at least one of said sources,
   c) at least one detector which preferentially detects collimated radiation,
   d) substantial collimation of the radiation impinging upon one of said detectors, and
   e) mounting said probe a variable distance from the surface of said window.

16. The method of claim 14 wherein specular reflection by said window from said sources to said detectors is reduced by means of at least one of the following:
   a) at least one source which emits substantially collimated radiation,
   b) substantial collimation of the radiation emitted by at least one of said sources,
   c) at least one detector which preferentially detects collimated radiation,
   d) substantial collimation of the radiation impinging upon one of said detectors, and
   e) mounting said probe a variable distance from the surface of said window.

17. The method of claim 1 wherein the temporal waveform of radiation emitted by each of said sources is distinctly chosen, whereby the contributions to any of said signals due to any of said sources can be separated.

18. The method of claim 1 wherein the influence of background radiation on said detected signals is reduced by at least one of the following:
   a) measuring said signals with said sources turned off, and subtracting these from said signals measured with said sources turned on,
   b) controlling the temporal waveform of radiation emitted by each of said sources in order to produce signal waveforms that can be distinguished from the signal waveforms caused by said background radiation,
   c) placing filters in front of said detectors whose transmittance is substantially less for said background radiation than for radiation originating from said sources.

19. The method of claim 1 wherein said radiation sources include at least one source emitting radiation within the visible to near infrared wavelength regions.

20. The method of claim 19 wherein said radiation sources include at least one additional source emitting radiation within the millimeter to microwave wavelength regions.

21. The method of claim 20 wherein said medium contains at least two particle types differing in relative size or other properties that affect their interaction with radiation, and wherein said parameter being determined is the concentration of at least one of these particle types.

22. The method of claim 1 wherein said sources include sources emitting radiation in at least two different regions of the electromagnetic spectrum.

23. The method of claim 22 wherein the different emission wavelengths of said sources are chosen such that at least one of said emission wavelengths lies substantially within a wavelength region of radiation absorption by a component of the medium, and at least one additional emission wavelength lies substantially outside of wavelength regions of radiation absorption by said component of the medium.

24. The method of claim 23 wherein said component is water and wherein the average path length of radiation traveled in the medium is one of said parameters being determined.

25. The method of claim 24 wherein the average path length of radiation traveled in the medium is used to determine the biomass present in the medium.

26. A method of determining the concentration of at least one type of particle in a medium which comprises the steps of:
   a) passing electromagnetic or acoustic radiation originating from each of a plurality of sources through said medium to a plurality of detectors;
   b) measuring a plurality of signals corresponding to the portion of radiation detected by each of said detectors that originated from each of said sources;

c) selecting signals from a group consisting of all of said signals, and combining the selected signals in a manner that, compared to said signals considered separately, improves the linearity of the combined result to changes in the logarithm of particle concentration; wherein the selection of signals and said combining of the selected signals is carried out at least once, whereby at least one said combined result is produced; and d) relating at least one of said combined results to said concentration of at least one type of particle.

27. The method of claim 26 wherein, compared to said signals considered separately, said combined result has substantially reduced the sensitivity to all of the following factors:

intensity of said radiation sources, sensitivity of said detectors, coupling efficiency of radiation from said radiation sources into said medium, and coupling efficiency of radiation from said medium to said detectors.

28. The method of claim 26 wherein step (a.) is accomplished by mounting a probe externally to a container that holds said medium, said container providing a window into said medium that is substantially transparent to the radiation emitted by said sources.

29. The method of claim 28 wherein the influence of the thickness of said window on the determined value of said parameters is reduced by including at least one of the following:

a) at least one source which emits substantially collimated radiation, b) substantial collimation of the radiation emitted by at least one of said sources, c) at least one detector which preferentially detects collimated radiation, d) substantial collimation of the radiation impinging upon one of said detectors, and e) a means of mounting said probe a variable distance from the surface of said window.

30. A method of determining the concentration of at least one type of particle in a medium which comprises the steps of:

a) passing electromagnetic or acoustic radiation originating from each of a plurality of sources through said medium to a plurality of detectors;

b) measuring a plurality of signals corresponding to the portion of radiation detected by each of said detectors that originated from each of said sources;

c) selecting signals from a group consisting of all of said signals, and combining the selected signals in a manner that, compared to said signals considered separately, increases the dynamic range over which particle concentration can be measured; wherein the selection of signals and said combining of the selected signals is carried out at least once, whereby at least one said combined result is produced; and d) relating at least one of said combined results to said concentration of at least one type of particle.

31. The method of claim 30 wherein, compared to said signals considered separately, said combined result has substantially reduced the sensitivity to all of the following factors:

intensity of said radiation sources, sensitivity of said detectors, coupling efficiency of radiation from said radiation sources into said medium, and coupling efficiency of radiation from said medium to said detectors.

32. The method of claim 30 wherein step (a.) is accomplished by mounting a probe externally to a container that holds said medium, said container providing a window into said medium that is substantially transparent to the radiation emitted by said sources.

33. The method of claim 32 wherein the influence of the thickness of said window on the determined value of said parameters is reduced by including at least one of the following:

a) at least one source which emits substantially collimated radiation, b) substantial collimation of the radiation emitted by at least one of said sources, c) at least one detector which preferentially detects collimated radiation, d) substantial collimation of the radiation impinging upon one of said detectors, and e) a means of mounting said probe a variable distance from the surface of said window.

34. A device for determining at least one parameter of a medium comprising:

a) a probe comprising a plurality of radiation sources that pass radiation through said medium to a plurality of detectors;

b) a controller for controlling said radiation sources, and measuring a plurality of signals corresponding to the portion of radiation detected by each of said detectors that originated from each of said radiation sources;

c) a processor for selecting signals from a group consisting of all of said signals, and combining the selected signals in a manner that substantially reduces the sensitivity of the combined result to all of the following factors as compared to said signals considered separately:

intensity of said sources, sensitivity of said detectors, coupling efficiency of radiation from said sources into said medium, and coupling efficiency of said radiation from said medium to said detectors;

wherein said selected signals comprise the signals collected from a plurality of said detectors, each detecting radiation that originated from a plurality of said sources, the separations between said sources and said detectors including at least three unique distances;

wherein the selection of signals and said combining of the selected signals is carried out at least once whereby at least one said combined result is produced; and relating at least one of said combined results to said at least one parameter of the medium.

35. The device of claim 34 wherein all of said sources and all of said detectors are stationary relative to each other.

36. The device of claim 34 wherein said radiation sources are each substantially monochromatic.

37. The device of claim 36 wherein said plurality of sources emit radiation of substantially identical wavelength.

38. The device of claim 34 wherein said sources and said detectors are arranged such that substantially only scattered radiation is detected by said detectors.

39. The device of claim 34 wherein said at least one parameter being determined is related to at least one of the concentration of at least one type of particle suspended in said medium, the average size of particles suspended in said medium, the size distribution of particles suspended in said medium, the chemical composition of particles suspended in said medium, the shape of particles suspended in said medium, and the chemical composition of said medium.

40. The device of claim 39 wherein said medium is a liquid culture containing a suspension of cells or microorganisms.

41. The device of claim 40 wherein at least one of the parameters is used to control at least one process variable that affects the growth of said cells or microorganisms.

42. The device of claim 34 wherein the accuracy of said parameter determination is improved by at least one of:
   a) influencing the intensity of radiation emitted from at least one of said sources to bring at least one of said signals within some optimum range;
   b) influencing the amplification of the signal collected from at least one of said detectors to bring at least one of said signals within some optimum range.

43. The device of claim 34 wherein said probe is immersed within said medium.

44. The device of claim 34 wherein said probe is mounted externally to a container that holds said medium, said container providing a window into said medium that is substantially transparent to the radiation emitted by said sources.

45. The device of claim 44 wherein the influence of the thickness of said window on the determined value of said parameters is reduced by including at least one of the following:
   a) at least one source which emits substantially collimated radiation,
   b) substantial collimation of the radiation emitted by at least one of said sources,
   c) at least one detector which preferentially detects collimated radiation,
   d) substantial collimation of the radiation impinging upon one of said detectors, and
   e) a means of mounting said probe a variable distance from the surface of said window.

46. The device of claim 44 wherein specular reflection by said window from said sources to said detectors is reduced by means of at least one of the following:
   a) at least one source which emits substantially collimated radiation,
   b) substantial collimation of the radiation emitted by at least one of said sources,
   c) at least one detector which preferentially detects collimated radiation,
   d) substantial collimation of the radiation impinging upon one of said detectors, and
   e) mounting said probe a variable distance from the surface of said window.

47. The device of claim 34 wherein the temporal waveform of radiation emitted by each of said sources is distinctly chosen, whereby the contributions to any of said signals due to any of said sources can be separated.

48. The device of claim 34 wherein the influence of background radiation on said detected signals is reduced by at least one of the following:
   a) measuring said signals with said sources turned off, and subtracting these from said signals measured with said sources turned on,
   b) controlling the temporal waveform of radiation emitted by each of said sources in order to produce signal waveforms that can be distinguished from the signal waveforms caused by said background radiation,
   c) placing filters in front of said detectors whose transmittance is substantially less for said background radiation than for radiation originating from said sources.

* * * * *